(12) United States Patent
Di Fabio

(10) Patent No.: US 6,413,985 B1
(45) Date of Patent: Jul. 2, 2002

(54) TETRAHYDROQUINOLINE DERIVATIVES AS GLYCINE ANTAGONISTS

(75) Inventor: Romano Di Fabio, Verona (IT)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 09/990,513

(22) Filed: Nov. 16, 2001

Related U.S. Application Data

(63) Continuation of application No. 09/719,188, filed as application No. PCT/EP99/03936 on Jun. 8, 1999.

(30) Foreign Application Priority Data

Jun. 10, 1998 (GB) ............................................. 9812408
Jun. 10, 1998 (GB) ............................................. 9812410

(51) Int. Cl.[7] ...................... A61K 31/47; C07D 215/02
(52) U.S. Cl. ...................... 514/314; 546/165; 546/167
(58) Field of Search .................. 514/314; 546/165, 546/167

(56) References Cited

U.S. PATENT DOCUMENTS 5,231,102 A    7/1993    Baker et al.

FOREIGN PATENT DOCUMENTS

| WO | WO 97/12870 A | 4/1997 |
|----|---------------|--------|
| WO | WO 98/07704 A | 2/1998 |
| WO | 99/64411 | * 12/1999 |

* cited by examiner

*Primary Examiner*—D. Margaret Seaman
(74) *Attorney, Agent, or Firm*—Lorie Ann Morgan

(57) ABSTRACT

The present invention provides compounds of formula (I)

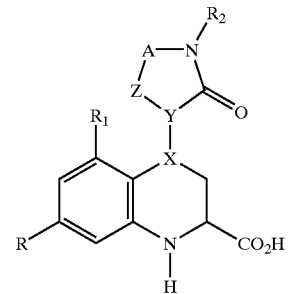

or a salt or a non-toxic metabolically labile ester thereof, processes for their preparation, pharmaceutical compositions containing the same and to their use in medicine.

10 Claims, No Drawings

TETRAHYDROQUINOLINE DERIVATIVES AS GLYCINE ANTAGONISTS

This Application is a continuation of U.S. patent application Ser. No. 09/719,188, filed Feb. 15, 2001 now allowed, which was filed pursuant to 35 U.S.C. §371 as a United States National Phase Application of International Application No. PCT/EP99/03936, filed Jun. 8, 1999, which claims priority to Great Britain Priority Patent Application Serial No. 9812410.0, filed Jun. 10, 1998 and Great Britain Priority Patent Application Serial No. 9812408.4, filed June 10, 1998.

This invention relates to 1, 2, 3, 4 tetrahydroquinoline derivatives, to processes for their preparation, to pharmaceutical compositions containing them and to their use in medicine. In particular, it relates to 1, 2, 3, 4 tetrahydroquinoline derivatives which are potent and specific antagonists of excitatory amino acids.

Carling et al., Bioorganic and Medicinal Chemistry Letters, Vol. 13 pp. 65–70, 1993, teaches 4-substituted-2-carboxy tetrahydroquinolines having good in vitro affinity for the glycine modulatory site of the NMDA receptor complex but at best only weak in vivo activity. More particularly, it teaches that such derivatives substituted at the 4 position by the group $CH_2CO_2H$ or $CH_2CONHPh$ have little or no in vivo activity when administered systemically (ip).

WO 97/12870 and WO 98107704 describe novel 4-substituted-2-carboxy-tetrahydroquinoline derivatives which not only have a good in vitro affinity for the strychnine insensitive glycine binding site associated with the NMDA receptor complex but also have good in vivo activity when administered intravenously (iv).

We have now discovered a novel group of 4-substituted-2-carboxy tetrahydroquinoline having a particularly useful profile of activity as selective antagonists for the strychnine insensitive glycine binding site associated with the NMDA receptor complex.

Thus the present invention provides a compound of formula (I)

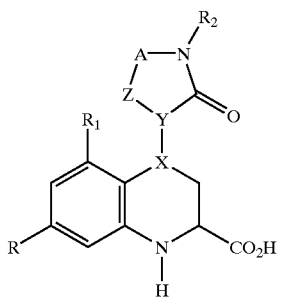

(I)

or a salt or a non toxic metabolically labile esters thereof, wherein

Y represents a carbon atom;

Z is the group CH which is linked to the group Y via a double bond and

X is CH or Z is methylene or $NR_{11}$ and X is a carbon atom linked to the group Y via a double bond;

A represents a $C_{1-2}$alkylene chain and which chain may be substituted by one or two groups selected from $C_{1-6}$alkyl optionally substituted by hydroxy, amino, $C_{1-4}$ alkyl amino or $C_{1-4}$dialkyl amino or which chain may be substituted by the group=0;

R represents a halogen atom or $C_{1-4}$alkyl group;

$R_1$ represents a hydrogen, a halogen atom or $C_{1-4}$alkyl group;

$R_2$ represents phenyl which may be substituted with up to 3 groups selected from halogen, hydrogen, or $(CH_2)_nR_3$ wherein $R_3$ is $COR_4$, $NR_6R_5$, $NHCOR_7$, $NHCONR_9R_8$ or $NH SO2 R_{10}$ group or $R_2$ is a 5 membered heteroaryl group containing 1 to 3 heteroatoms selected from oxygen, sulphur and nitrogen; or 6 membered heteroaryl group containing 1 to 3 nitrogen atoms $R_4$ represents an amino, a hydroxyl or $C_{1-4}$ alkoxy group;

$R_5$ and $R_6$ each independently represents hydrogen or $C_{1-4}$ alkyl group or $R_5$ and $R_6$ together with the nitrogen atom to which they are attached represent a saturated 5–7 membered heterocyclic group optionally containing an additional heroatom selected from oxygen,sulphur or nitrogen $R_7$ represents a hydrogen atom or $C_{1-4}$ alkyl, $C_{1-4}$ alkoxy, or phenyl;

$R_8$ represents hydrogen or $C_{1-4}$ alkyl group;

$R_9$ represents hydrogen, optionally substituted $C_{1-4}$ alkyl (optionally substituted by one or more hydroxy carboxyl and amino group), phenyl;

$R_{11}$ represents hydrogen or $C_{1-4}$ alkyl group;

$R_{10}$ represents hydrogen, $C_{1-4}$ alkyl or a nitrogen protecting group.

n is zero or an integer from 1 to 2;

A further embodiment of the invention provides compounds of formula(I)or a salt or a non toxic metabolically labile esters thereof, wherein Y represents a carbon atom;

Z is the group CH which is linked to the group Y via a double bond and

X is CH or Z is methylene or $NR_{11}$ and X is a carbon atom linked to the group Y via a double bond;

A represents a $C_{1-2}$ alkylene chain and which chain may be substituted by one or two groups selected from $C_{1-4}$ alkyl optionally substituted by hydroxy, amino, $C_{1-4}$ alkyl amino or $C_{1-4}$ dialkyl amino or which chain may be substituted by the group=0;

R represents a halogen atom;

$R_1$ represents a hydrogen or a halogen atom;

$R_2$ represents phenyl which may be substituted with up to 3 groups selected from halogen, hydrogen, or $(CH_2)_nR_3$ wherein $R_3$ is $COR_4$, $NR_6R_5$, $NHCOR_7$, $NHCONR_9R_8$ or $NH SO2 R_{10}$ group or $R_2$ is a 5 membered heteroaryl group containing 1 to 3 heteroatoms selected from oxygen, sulphur and nitrogen; or 6 membered heteroaryl group containing 1 to 3 nitrogen atoms $R_4$ represents an amino or a hydroxyl;

$R_5$ and $R_6$ each independently represents hydrogen or $C_{1-4}$ alkyl group or $R_5$ and $R_6$ together with the nitrogen atom to which they are attached represent a saturated 5–7 membered heterocyclic group optionally containing an additional heroatom selected from oxygen,sulphur or nitrogen $R_7$ represents a hydrogen atom or $C_{1-4}$, alkyl, $C_{1-4}$ alkoxy, or phenyl;

$R_8$ represents hydrogen or $C_{1-4}$ alkyl group;

$R_9$ represents hydrogen, optionally substituted $C_{1-4}$ alkyl (optionally substituted by one or more hydroxy carboxyl and amino group), phenyl;

$R_{11}$ represents hydrogen or $C_{1-4}$ alkyl group;

$R_{10}$ represents hydrogen, $C_{1-4}$ alkyl or a nitrogen protecting group;

n is zero or an integer from 1 to 2 with the proviso that when X is a carbon atom linked to the group Y via a double bond then $R_1$ is hydrogen;

For use in medicine the salts of the compounds of formula (I) will be physiologically acceptable thereof. Other salts however may be useful in the preparation of the compounds of formula (I) or physiologically acceptable salts thereof. Therefore, unless otherwise stated, references to salts include both physiologically acceptable salts and non-physiologically acceptable salts of compounds of formula (I).

Suitable physiologically acceptable salts of compounds of the invention include base addition salts and, where appropriate, acid addition salts. Suitable physiologically acceptable base addition salts of compounds of formula (I) include alkali metal or alkaline metal salts such as sodium, potassium, calcium, magnesium and ammonium salts, formed with amino acids (e.g. lysine and arginine) and organic bases (e.g. procaine, phenylbenzylamine, ethanolamine diethanolamine and N-methyl glucosamine).

The compounds of formula (I) and/or salts thereof may form solvates (e.g. hydrates) and the invention includes all such solvates.

The term halogen refers to a fluorine, chlorine, bromine or iodine atom.

The term $C_{1-4}$ alkyl as used herein as a group or part of a group refers to a straight or branched chain alkyl group containing from 1 to 4 carbon atom, examples of such groups include methyl, ethyl, propyl, isopropyl, n-butyl, isobutyl, secondary butyl or tertiary butyl.

When $R_2$ is a 5 or 6 membered heteroaryl group this may be for example furanyl, thiophenyl, imidazolyl, thiazolyl, oxazolyl, pyridyl or pyrimidinyl.

When $R_5$ and $R_6$ together with the nitrogen atom to which they are attached form a saturated 5–7 membered heterocyclic group optionally containing an additional heroatom selected from oxygen, sulphur or nitrogen this may be morpholino, 2,6 dimethylmorpholino, thiomorpholino, piperidino, pyrrolidino, piperazino or N-methylpiperazino.

When $R_2$ is a substituted phenyl group this is conveniently a mono substituted phenyl group. The substituent is conveniently in the meta position or more conveniently in the para position.

When X—Y represents a double bond, the compounds of formula (I) possess at least one asymmetric carbon atom (namely the carbon atom occupying the 2 position of the 1, 2, 3, 4 tetrahydroquinoline ring system) and other asymmetric carbon atoms are possible in the group $R_2$. It is to be understood that all enantiomers and diastereomers and mixtures thereof are encompassed within the scope of the present invention.

When X—Y represents a single bond, the compounds of formula (I) possess at least two asymmetric carbon atoms (namely the carbon atom occupying the 2 and 4 position of the 1, 2, 3, 4 tetrahydroquinoline ring system) and these may be represented by the formulae (1a, 1b, 1c and 1d).

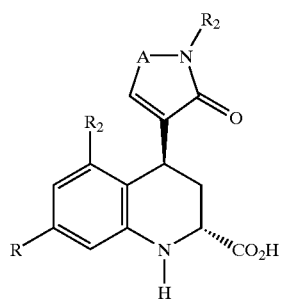

(1a)

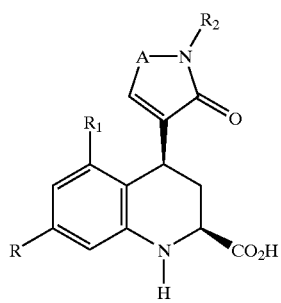

(1b)

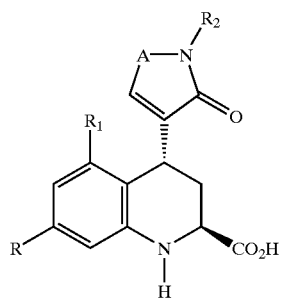

(1c)

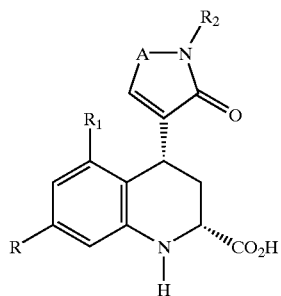

(1d)

The solid wedge shaped bond indicates that the bond is above the plane of the paper and is referred to as the β configuration. The broken indicates that the bond is below the plane of the paper and is referred to as α configuration.

Further other asymmetric carbon atoms are possible in the groups $R_2$. It is to be understood that all enantiomers and diastereomers and mixtures thereof are encompassed within the scope of the present invention.

Nonoxic metabolically labile esters of compound of formula (I) are esters of compounds of formula (I) that are hydrolysed in vivo to afford said compound of formula I and a physiologically acceptable alcohol. Non toxic metabolically esters of compound of formula (I) may be formed by esterification, for example of any of the carboxylic acid groups in the parent compound of general formula (I) with, where appropriate, prior protection of any other reactive groups present in the molecule, followed by deprotection if required. Examples of such metabolically labile esters include $C_{1-4}$alkyl esters e.g. methyl or ethyl esters, substituted or unsubstituted aminoalkyl esters (e.g. aminoethyl, 2-(N,N-diethylamino) ethyl, or 2-(4-morpholino)ethyl esters or acloxyalkyl esters such as, acyloxymethyl or 1-acyloxyethyl e.g. pivaloyloxymethyl, 1-pivaloyloxyethyl, acetoxymethyl, 1-acetoxyethyl, 1-(1-methoxy-1-methyl) ethylcarbonyloxyethyl, 1-benzoyloxyethyl, isopropoxycarbonyloxymethyl, 1-sopropoxycarbonyloxyethyl, cyclohexylcarbonyloxymethyl, 1-cyclohexylcarbonyloxyethyl ester, cyclohexyloxycarbonyloxymethyl, 1-cyclohexyloxycarbonyloxyethyl, 1-(4-tetrahydropyranyloxy)carbonyloxyethyl or 1-(4-tetrahydropyranyl)carbonyloxyethyl.

The group R is conveniently chlorine.

The group $R_1$ is conveniently a hydrogen or a chlorine atom.

A preferred class of compounds of formula(I) is that wherein R is chlorine and $R_1$ is a hydrogen or a chlorine atom.

A further preferred class of compounds of formula(I) is that wherein R is chlorine and $R_1$ is a hydrogen atom.

When X—Y is a single bound, a preferred class of compounds of formula (1) is that in which the carbon atom in 4 position is $\beta$ configuration and the carbon atom in 2 positition is in a configuration (1a) and that in which the carbon atom in 4 position is a configuration and the carbon atom in 2 position is in $\beta$ configuration (1c).

When A is an optionally substituted $C_{1-2}$ alkylene chain this may be, for example, methylene, ethylene or C=O.

A preferred class of compounds of formula (I) includes those wherein A is a chain selected from —CH2—, —(CH$_2$)2—, C=O.

When Z is a group $NR_{11}$ this is conveniently the group NH.

A preferred class of compounds of formula (I) includes those wherein Z is CH which is linked to the group Y via a double bond a methylene or a NH group.

When $R_2$ is an optionally substituted phenyl group this is conveniently phenyl substituted by a single substituent selected from $(CH_2)_nNR_6R_5$ in which $R_5$ is hydrogen and $R_6$ is hydrogen, $C_{1-4}$ alkyl (e.g. methyl, ethyl) or $NR_6R_5$ represents a saturated 6 membered ring containing oxygen e.g. morpholino; $(CH_2)_nNHCOR_7$ wherein $R_7$ is hydrogen, alkyl e.g. methyl, isopropyl, isobutyl, phenyl; $(CH_2)_nNHCONHR_9$ wherein $R_9$ is hydrogen; $(CH_2)_nNH SO2 R_{10}$ in which $R_{10}$ is alkyl e.g. methyl. n is zero or an integer from 1 to 2; Examples of such $R_2$ groups include phenyl (optionally substituted by amino, t-butoxycarbonylamino, acetylamino or methanesulphonylamino).

When $R_2$ is substituted phenyl the substituents are conveniently in the meta or more preferably in the para position.

When $R_2$ is a 5 or 6 membered heteroaryl group as above defined this is conveniently pyridyl e.g. 3-pyridyl.

A preferred class of compounds of formula (I) is that wherein $R_2$ represents phenyl (optionally substituted by acetylamino, methanesulphonylamino) or 3-pyridyl. Within this class those wherein $R_2$ is phenyl are particularly preferred.

A further preferred class of compounds of formula (I) is that wherein X is a carbon atom linked to the group Y via a double bond.

A preferred group of compounds of formula(I) is that wherein A is is a chain selected from —CH$_2$— or —(CH$_2$)$_2$—, Z is a group CH which is linked to the group Y via a double bond or a methylene group, or A is the chain CO and Z is an NH group, R is chlorine, $R_1$ is chlorine or hydrogen and $R_2$ is phenyl (optionally substitued by acetylamino or methanesulphonylamino) or 3-pyridyl.

Specific preferred compounds of the invention include:
(±)7-chloro-4-2-oxo-1-phenyl-3-pyrrolidinylidene)-1,2,3,4-tetrahydro-2-quinoline carboxylic acid,
(±)7-chloro-4-(1-phenyl-$\Delta^3$-pyrrolin-2-one-3yl)-1,2,3,4-tetrahydro-2-quinoline carboxylic acid,
and physiologically acceptable salts (e.g. sodium salt) non-toxic metabolically labile esters or enantiomers thereof.
(−)-Sodium 7-chloro-4-(2-oxo-1-phenyl-3-pyrrolidinylidene)-1,2,3,4-tetrahydro-2-quinolinecarboxylate.
(−)Sodium 7-chloro-4(1-phenyl-$\Delta^3$-pyrrolin-2-one-3yl)-1,2,3,4-tetrahydroquinoline-2-carboxylate,
(+)Sodium 7-chloro-4-(1-phenyl-$\Delta^3$-pyrrolin-2-one-3yl)-1,2,3,4-tetrahydroquinoline-2carboxylate.

Further specific preferred compounds of the invention include:
(±)-7-chloro-4-(1-(3-pyridin)-$\Delta^3$-pyrrolin-2-one-3yl)-1,2,3,4-tetrahydroquinoline-2-carboxylic acid,
(±)-7-chloro-4-(1-phenyl$\Delta^3$-5,6-dihydro-pyridin-2-one-3yl)-1,2,3,4-tetrahydroquinoline-2-carboxlic acid,
(±)-5,7dichloro-4-(1-phenyl-$\Delta^3$-pyrrolin-2-one-3yl)-1,2,3,4-tetrahydroquinoline-2carboxylic acid,
(+/−)-7chloro-4-(1-(4-acetylamino)-1-phenyl-$\Delta^3$-pyrrolin-2-one-3yl)-1,2,3,4-tetrahydroquinoline-2-carboxylic acid,
(+/−)7-chloro-4(1-(4-methanesulfonylamino)-1-phenyl-$\Delta^3$-pyrrolin-2-one-3yl)-1,2,3,4-tetrahydroquinoline-2-carboxylic acid,
(±)-7-chloro-4-(2-oxo-1-phenyl-3-piperidinylidene)-1,2,3,4-tetrahydro-2-quinolinecarboxylic acid,
(±)-7-chloro-4-(2,5-dioxo-1-phenyl-imidazolidin-4-ylidene)-1,2,3,4-tetrahydro-2-quinolinecarboxylic acid,
(±)-7-chloro-4(2-oxo-1-(pyridin-3yl)-pyrrolidin-3-ylidene)-1,2,3,4-tetrahydro-2quinolinecarboxylate,
(±)-7-chloro-4-(2-oxo-1-(4-acetylamino)phenyl-pyrrolidin-3-ylidene)-1,2,3,4-tetrahydro-2-quinolinecarboxylic acid,
(±)7-chloro-4-(2-oxo-1((4-methanesulfonyl amino)phenyl-pyrrolidin-3-ylidene)-1,2,3,4-tetrahydro-2-quinolinecarboxylic acid,
5,7-dichloro-4-(2-oxo-1-(phenyl)-pyrrolidin-3-ylidene)-1,2,3,4-tetrahydro-2quinoline carboxylic acid(enantiomer A);
5,7-dichloro-4-(2-oxo-1-phenyl-$\Delta$3-pyrrolin-2-one-3-yl)1,2,3,4-tetrahydroquinoline-2-carboxylic acid (enatiomer A);
and physiologically acceptable salts (e.g. sodium salts), non-toxic metabolically labile esters or enantiomers thereof.

The compounds of formula (I) and/or physiologically acceptable salts thereof are excitatory amino acid antagonists. More particularly they are potent antagonists at the strychnine insensitive glycine binding site associated with the NMDA receptor complex. As such they are potent antagonists of the NMDA receptor complex. These compounds are therefore useful in the treatment or prevention of neurotoxic damage or neurodegenerative diseases. Thus the compounds are useful for the treatment of neurotoxic injury which follows cerebral stroke, thromboembolic stroke, hemorrhagic stroke, cerebral ischemia, cerebral vasospam, hypoglycemia, amnesia, hypoxia, anoxia, perinatal asphyxia cardiac arrest. The compounds are useful in the treatment of chronic neurodegenerauive diseases such as: Huntingdon's disease, Alzheimer's senile dementia, amyotrophic lateral sclerosis, Glutaric Acidaemia type, multi-infarct dementia, status epilecticus, contusive injuries (e.g. spinal cord injury and head injury), viral infection induced neurodegeration (e.g. AIDS, encephalopaties), Down syndrome, ocular neurodegeneration (e.g glaucoma), epilepsy, schizophrenia, depression, migraine, headaches including cluster headaches and or tension headaches, anxiety, pain (e.g inflamatory pain and neuropathic pain), neurogenic bladder, emesis irritative bladder disturbances, drug dependency, including withdrawal symptoms from alcohol, cocaine, opiates, nicotine (e.g. smoking cessation) benzodiazepines and. inhibition of tolerance induced by opioids (i.e morphine).

The potent and selective action of the compound of the invention at the strychnine-insensitive glycine binding site present on the NMDA receptor complex may be readily determined using conventional test procedures. Thus the ability to bind at the strychnine insensitive glycine binding site was determined using the procedure of Kishimoto H et al., J Neurochem 1981, 37, 1015–1024. The selectivity of the action of compounds of the invention for the strychnine insensitive glycine site was confirmed in studies at other ionotropic known excitatory amino acid receptors. Thus compounds of the invention were found to show little or no affinity for the kainic acid (kainate) receptor, a-amino-3-hydroxy-5-methyl-4-isoxazole-proprionic acid (AMPA) receptor or at the NMDA binding site.

Compounds of the invention may be found found to inhibit NMDA induced convulsions in mice using the procedure Chiamulera C et at, Psychopharmacology (1990), 102, 551–552.

The neuroprotective activity of the compounds of the invention may be demonstrated in the middle cerebral artery occlusion preparation in mice, using the procedure described by Chiamulera C. et al., European Journal of Pharmacology, 216 (1992) pp. 335–336.

The ability of compounds of the invention to alleviate withdrawal symptoms from nicotine following smoking cessation may be demonstrated in conventional tests of nicotine induced relapse using the procedure described in C. Chiamulera et al., Arch. Pharmacol., 358, 1998.

The invention therefore provides for the use of a compound of formula (I) and/or physiologically acceptable salts or non-toxic metabolically labile esters thereof for use in therapy and in particular use as medicine for antagonising the effects of excitatory amino acids upon the NMDA receptor complex.

The ability of compounds of the invention to inhibit pain may be demonstrated in conventional analgesic screen such as those described by Dubuisson and Dennis, *Pain,* 1977, 4:161–174; J. J. Bennett and J. K Xue, *Pain,* 1988, 41, 87–107.

The invention also provides for the use of a compound of formula (I) and/or a physiologically acceptable salt or non-toxic metabolically labile esters thereof for the manufacture of a medicament for antagonising the effects of excitatory amino acids upon the NMDA receptor complex.

According to a further aspect, the invention also provides for a method for antagonising the effects of excitatory amino acids upon the NMDA receptor complex, comprising administering to a patient in need thereof an antagonistic amount of a compound of formula (I) and/or a physiologically acceptable salt thereof.

It will be appreciated by those skilled in the art that reference herein to treatment extends to prophylactics as well as the treatment of established diseases or symptoms.

It will further be appreciated that the amount of a compound of the invention required for use in treatment will vary with the nature of the condition being treated, the route of administration and the age and the condition of the patient and will be ultimately at the discretion of the attendant physician. In general however doses employed for adult human treatment will typically be in the range of 2 to 800 mg per day, dependent upon the route of administration. Thus for parenteral administration a daily dose will typically be in the range 20–100 mg, preferably 60–80 mg per day. For oral administration a daily dose will typically be within the range 200–800 mg , e.g. 400–600 mg per day.

The desired dose may conveniently be presented in a single dose or as divided doses administered at appropriate intervals, for example as two, three, four or more sub-doses per day.

While it is possible that, for use in therapy, a compound of the invention may be administered as the raw chemical, it is preferable to present the active ingredient as a pharmaceutical formulation.

The invention thus further provides a pharmaceutical formulation comprising a compound of formula (I) or a pharmaceutically acceptable salt or non-toxic metabolically labile esters thereof together with one or more pharmaceutically acceptable carriers thereof and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, inhalation or insufflation, implant or rectal administration.

Tablets and capsules for oral administration may contain conventional excipients such as binding agents, for example, syrup, acacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate, or wetting agents such as sodium lauryl sulphate. The tablets may be coated according to methods well known in the art. Oral liquid preparations may be in the form of, for example, aqueous or oily suspensions, solutions emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan monooleate or acacia; non-aqueous vehicles (which may include edible oils), for example, almond oil, fractionated coconut oil, oily esters, propylene glycol or ethyl alcohol; solubilizers such as surfactants for example polysorbates or other agents such as cyclodextrins; and preservatives, for example, methyl or propyl p- hydroxybenzoates or ascorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by injection or continuous infusion. Formulations for injection may be presented in unit dose form in ampoules, or in multidose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

For administration by inhalation the compounds according to the invention are conveniently delivered in the form of an aerosol spray presentation from pressurised packs, with the use of a suitable propellant, such as dichlorodifluoromethane, tirchlorofluoromethane, dichlorotetrafluoroethane, carbon dioxide or other suitable propellants, such as dichlorodifluoromethane, trichlorofluoromethane, dichlorotetrafluoroethane, carbon dioxide or other suitable gases, or from a nebuliser. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable carrier such as lactose or starch. The powder composition may be presented in unit dosage form in, for example, capsules or cartridges of e.g. gelatin, or blister packs from which the powder may be administered with the aid of an inhaler or insufflator.

The composition according to the invention may also be formulated as a depot preparation. Such long acting formulations may be administered by implantation (for example subcutaneously or intramuscularly) or by intramuscular injection. Thus for example, the compounds of the invention may be formulated with suitable polymeric or hydrophobic materials (for example as an emulsion in an acceptable oil) or ion exchange resins, or as sparingly soluble derivatives, for example, as a sparingly soluble salt The compositions according to the invention may contain between 0.1–99% of the active ingredient, conveniently from 30–95% for tablets and capsules and 3–50% for liquid preparations.

Compounds of general formula (I) enantiomers and salts thereof may be prepared by the general methods outlined hereinafter. In the following description, the groups R, $R_1$, $R_2$, A, Z, X and Y are as defined for the compounds of formula (I) unless otherwise stated.

Compounds of formula (I) and enantiomers thereof may be prepared by the cyclisation of a compound of formula (II) in which $R_{12}$ is a carboxylic protecting group, $R_{13}$ represents a bromine or iodine atom, $R_{14}$ represents hydrogen or a nitrogen protecting group.

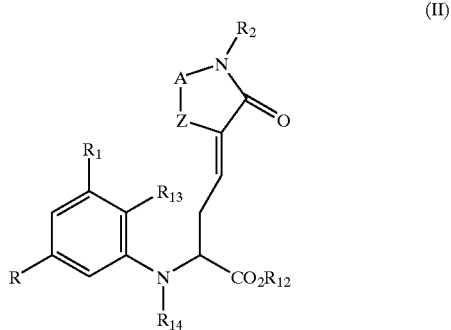

(II)

Followed where necessary or desired by removal of one or more protecting groups.

In one embodiment of this process the reaction may be carried out using a catalytic amount of a Palladium (O) complex such as tetrakis(triphenylphosphine)palladium and a suitable organic base such as trialkylamine e.g. triethylamine or inorganic base, e.g. potassium carbonate.

The reaction is conveniently carried out in an aprotic polar solvent such as acetonitrile, dimethylformamide or in aprotic apolar solvent such as hydrocarbon (ie toluene, xilene, hexane) at a temperature within the range of 60° C. to 150° C. followed, where necessary or desired, by subsequent removal of the carboxyl protecting group $R_{12}$ and any protecting group $R_{14}$.

In a further embodiment of the process the reaction is carried out using a catalytic amount of a Pd(II) salt such as: palladium acetate or palladium dichloride in the presence of a suitable organic base such as trialkyl amine e.g. triethylamine and of a triarylphosphine such as triphenylphosphine.

The reaction is carried out in an aprotic solvent such as acetonitrile or dimethylformamide and preferably with heating followed, where necessary or desired, by subsequent removal of the carboxyl protecting group $R_{12}$ and any nitrogen protecting group $R_{14}$.

Compounds of formula (I) wherein X—Y is a double bond may be regioselectively prepared by carring out the cyclisation reaction in an aprotic apolar solvent such as toluene in the presence of catalytic amount of a Palladium (O) complex such as tetrakis(triphenylphosphine)palladium and a suitable organic base such as trialkylamine e.g. triethylamine or inorganic base, e.g. potassium carbonate. Compounds of formula (I) wherein X—Y is a single bond may be prepared by carring out the reaction the cyclisation reaction in an aprotic polar solvent (such as acetonitrile, dimethylformamide) in the presence of a catalytic amount of a Pd(II) salt such as: palladium acetate or palladium dichloride in the presence of a suitable organic base such as trialkyl amine e.g. triethylamine and of a triarylphosphine such as triphenylphosphine.

Suitable carboxyl protecting groups $R_{12}$ for use in this reaction include alkyl, such as ethyl, trichloroalkyl, trialkylsilylalkyl, or arylmethyl groups such as benzyl, nitrobenzyl or trityl. Further convenient carboxyl protecting groups are those having a chiral group derived from chiral alcohols such as (+)-S-indanol, (+)-S-methyl mandelate, chiral ($C_{1-4}$)alkyl lactate: i.e. (+)-R- or (−)-S-methly lactate, (+)-R-t-butyl lactate, (+)-R- or (-4thyl lactate, (−)-S4-isopropyl lactate, (−)-S-butyl lactate, (+)-R-isobutyl lactate or chiral aralkyl lactate (i.e. benzyl lactate), (−)-S-perillyl alcohol, (−)-methyl-(R)-3-hydroxy-2-methylpropionate, (−)-(R)-2-butanol, (−)-(S)-2-methyl-1-butanol. $R_{12}$ is preferably an ethyl, benzyl group or a group derived from a chiral($C_{1-4}$) alkyl lactate alcohol (eg (+)-(R)-t-butyl lactate (−)-S-butyl lactate, (+)-R-isobutyl lactate alcohol).

When $R_{14}$ is nitrogen protecting examples of suitable groups include alkoxycarbonyl e.g. t-butoxycarbonyl, arylsulphonyl e.g. phenysulphonyl or 2-trimethylsilylethoxymethyl. Compounds of formula (II) may be prepared from compound of formula (III) in which $R_{12}$ is a carboxyl protecting group and $R_{14}$ is hydrogen or a nitrogen protecting group as defined in formula (II) and $R_{13}$ represents a bromine or iodine atom.

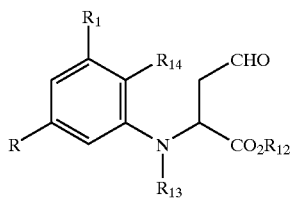

(III)

by reaction with an appropriate phosphorus reagent capable of converting the group CHO into the group:

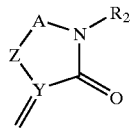

followed, where necessary or desired, by removal of the carboxyl protecting group $R_{12}$ and nitrogen protecting group $R_{13}$. In one embodiment of this process the reaction may be carried out using a phosorus ylide of formula (IV)

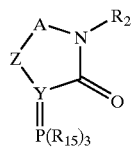

(IV)

wherein $R_{15}$ is an alkyl or phenyl group.

The reaction is carried out in an aprotic solvent such as acetonitrile or dimethylformamide at a temperature ranging from −20° C. to the reflux temperature of the solvent.

Compounds of formula (III) and (IV) are either known compounds or may be prepared by analogous methods to those used for known compounds. A convenient method for preparing compounds of formula (III) is reacting compound of formula (V) in which $R_{12}$ is a carboxyl protecting group and $R_{14}$ is hydrogen or a nitrogen protecting group as defined in formula (II) and $R_{13}$ represents a bromine or iodine atom with an allyltintrihalide.(VI) followed by ozonization reaction

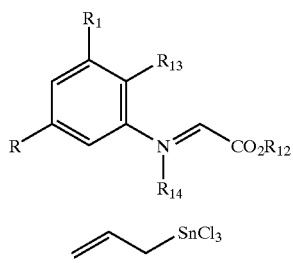

The reaction conveniently takes place in a solvent such as hydrocarbon e.g. Toluene or halogenated hydrocarbon (e.g. dichloro methane at a temperature ranging from −78° C. to room temperature). The ozonization may be carried out by passing a stream of ozone into a solution in the presence of dimethyl sulphide or triphenylphosphine in a suitable solvent such as halohydrocarbon (e.g dicholoromethane) at low temperature e.g. −78° C.

Alternatively compounds (III) may be prepared by aldolic reaction of the imino compound (V), with the enol ether (VII), wherein $R_{16}$ is a $C_{1-4}$ alkyl group.

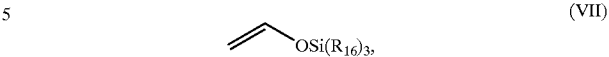

The reaction may be carried out in a solvent such as methylene cloruro or acetonitrile in the presence of a Lewis acid such as Ytterbium triflate.

In any of the above reactions the carboxyl protecting group may be removed by conventional procedures known for removing such groups. Thus compounds where $R_{12}$ is a benzyl, ethyl or (+)-R- or (−)-S-t-butyl lactate group may be removed by hydrolysis using an alkali metal hydroxide e.g. lithium hydroxide or sodium hydroxide in a suitable solvent such as ethanol or isopropanol, water or mixtures thereof, followed, where desired or necessary, by that addition of a suitable acid e.g. hydrochloric acid to give the corresponding free carboxylic acid.

In any of the above reactions the nitrogen protecting group may be removed by conventional procedures known for removing such groups, for example by acid or base hydrolysis. Thus when $R_{14}$ is alkoxycarbonyl e.g. t-butoxycarbonyl or phenylsulphonyl it may be removed by alkaline hydrolysis using for example lithium hydroxide in a suitable solvent such as tetrahydrofuran or an alkanol e.g. isopropanol. Alternatively the alkoxycarbonyl group may be removed by acid hydrolysis.

Physiologically acceptable salts of compounds of formula (I) may be prepared by treating the corresponding acid with an appropriate base in a suitable solvent For example the sodium or potassium salt may be prepared by treating a solution of the corresponding acid of a compound of formula (I) with sodium or potassium 2-ethylhexanoate with alkali or alkaline metal hydroxide, or the corresponding carbonate or bicarbonate thereof. Alternatively alkali or alkaline metal salts may be prepared by direct hydrolysis of carboxyl protected derivatives of compounds of formula (I) with the appropriate alkali or alkaline metal hydroxide.

Metabolically labile esters of compounds of formula (I) may be prepared by esterification of the carboxylic acid group or a salt thereof or by trans esterfication using conventional procedures. Thus, for example, acyloxyalkyl esters may be prepared by reacting the free carboxylic acid or a salt thereof with the appropriate acyloxylalkyl halide in a suitable solvent such as dimethylformamide. For the esterifcation of the free carboxyl group this reaction is preferably carried out in the presence of a quaternary ammonium halide such as tetrabutylammonium chloride or benzyltriethylammonium chloride.

Specific enantiomers of the compounds of formula (I) may also be obtained from corrisponding racemic compounds of formula (I) using chiral HPLC procedure.

Alternatively the enantomers may be prepared by esterification of the corresponding racemic compounds of formula (I) with a suitable chiral alcohol, separating the resultant diastereomeric esters by conventional means e.g. chromatography or crystallisation followed by hydrolysis of the diastereomeric esters.

Suitable chiral alcohols for use in the process include (+)-S-indanol, (+)-S-methyl mandelate, chiral $(C_{1-4})$alkyl lactate: i.e. (+)-R- or (−)-S-methly lactate, (+)-R-t-butyl lactate, (+)-R- or (−)-4-ethyl lactate, (−)-4-isopropyl lactate, (−)-S-butyl lactate, (+)-R-isobutyl lactate or chiral aralkyl lactate (i.e. benzyl lactate), (−)-S-perillyl alcohol, (−)methyl-(R)-3-hydroxy-2-methylpropionate, (−)-(R)-2-butanol, (−)-(S)-2-methyl-1-butanol.

The diastereomeric esters of compounds of formula (I) may be prepared by conventional means such as reaction of the chiral alcohol with an activated derivative of a compound of formula (I) in an aprotic solvent such as ether e.g. tetrahydrofuran. The activated derivative of a compound of formula (I) may be prepared from compounds (I) using conventional means for preparing activated derivatives of a carboxylic acid groups such as those conveniently used in peptide synthesis.

A particularly convenient method of preparing the diastereomeric esters of compounds (I) is to prepare the activated derivative of compounds (I) in the presence of the chiral alcohol.

Thus for example racemic mixture of compounds (I) may be treated with the Mitsunobu combination of reagents, i.e. a dialkyl azodicarboxylate such as diethylazodicarboxylate and a triarylphosphine e.g. triphenylphosphine or trialkylphoshine (i.e. tributylphosphine) in the presence of the chiral alcohol.

The reaction conveniently takes place in the presence of a suitable solvent such as an ether (e.g. diethylether or tetrahydrofuran), a halohydrocarbon (e.g. dichloromethane) or a nitrile (e.g. acetontrile) or a mixture thereof at a temperature ranging from 0–30° C.

The required single diastereomeric ester of compounds (I) may be obtained from the mixture thereof by conventional means, for example by the use of conventional chromatographic procedures such as preparative HPLC or by fractional crystallization. Alternatively the required single diastereomeric ester of compound of formula (I) may be obtained using a suitable chiral protecting group $R_{12}$ as defined in formula (II). Specific enantiomers of compounds of formula (I) may be prepared from the corresponding single diastereomeric ester of compounds (I) by hydrolysis e.g. alkaline hydrolysis. Thus, for example, the hydrolysis may be carried using an alkali metal hydroxide e.g. sodium hydroxide or lithium hydroxide in a solvent such as an ether e.g. tetrahydrofuran and water.

Alternatively specific enantiomers of compounds of formula (I) may be prepared by stereoselective enzymatic hydrolysis of compounds of formula (VIII)

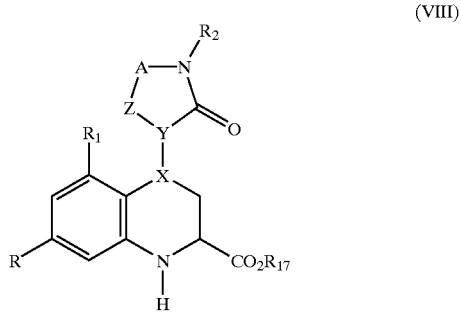

(VIII)

Wherein $R_{17}$ is a carboxyl protecting group Suitable carboxyl protecting group $R_{17}$ for use in this reaction include $C_{1-4}$ alkyl such as methyl, ethyl, propyl, butyl, or arylmethyl groups such as benzyl, nitrobenzyl or trityl. Suitable enzymes for use in this reaction are lipase enzymes such as *Aspergillus niger* (AP-12) ILipase-DS (*Aspergillus niger*, Amano), *Candida rugosa*lipase (Amano), *Candida cylindracea* lipase (Amano), Alcaligenes sp. lipase, *Rhizopus arrhizus* lipase (Biotal), Wheat germ lipase (Sigma), *Rhizopus niveus* lipase (Amano), Promod 215-P protease (Biocatalyst), lipase E-7 Themogen), lipase E-17 (Thermogen). Further suitable enzymes which may be used in this reaction are porcine pancreatic lipase, alpha-chymotrypsin or trypsin. A particular preferred enzyme for use in this reaction is *Aspergillus niger* (AP-12).

Resting cells of the following organisms may also be used in this reaction *Aspergillus ochraceus, Aspergillus niger, Aspergillus chevalied & Aspergillus cervinus*.

The reaction is conveniently carried out in an aprotic solvent such as DMSO, tetrahydrofuran in the presence of a suitable aqueous buffer (i.e. phosphate buffer or $CaCl_2$. If required a solubilising agent such as Tween-80 may be added to the reaction mixture. In a further process the enzyme may be immobilized and the reaction is carried out in essentially "neat" water-saturated organic solvents such as methyl tert-butyl ether or tert-amyl alcohol.

In order that the invention may be more fully understood the following examples are given by way of illustration only.

In the Intermediates and Examples unless otherwise stated: Melting points (m.p.) were determined on a Gallenkamp m.p. apparatus and are uncorrected. All temperatures refer to ° C. Infrared spectra were measured on a FT-IR instrument. Proton Magnetic Resonance ($^1$H-NMR) spectra were recorded at 400 MHz, chemical shifts are reported in ppm downfield (d) from $Me_4Si$, used as internal standard, and are assigned as singlets (s), doublets (d), doublets of doublets (dd), triplets (t), quartets (q) or multiplets (m). Column chromathography was carried out over silica gel (Merck AG Darmstaadt, Germany). The following abbreviations are used in text EA=ethyl acetate, CH=cyclohexane, DCM=dichloromethane, THF=tetrahydrofuran, TFA=trifluoroacetic acid, TEA=triethylamine, DMF=dimethylformamide, $Ac_2O$=acetic anhydride, PPA=polyphosphoric acid, DBU=1,8-diazobicyclo [5,4,0] undec-7-ene, DMSO=dimethylsulphoxide, IMS=mixture of Ethanol with 5% of methanol,LHDMS=Lithiumbis (trimethylsilyl)amide. DIPEA=diisopropylethylamine Tlc refers to thin layer chromatography on silica plates, and dried refers to a solution dried over anhydrous sodium sulphate; r.t. (RT) refers to room temperature. Enantiomer A or diastereoisomer A refer to a single enatiomer or a single diastereoisomer respectively whose absolute stereochemistry was not characterized.

Intermediate 1

(+)-Ethyl 2-(5-chloro-2-iodoanilino)-4-pentenoate

To a solution of 2-iodo 4 chloro aniline (9.1 g) in dry toluene (150 ml) ethyl glyoxylate (50% solution in toluene, 14.6 ml) and $MgSO_4$ (2 g) were added and the resulting suspension was refluxed overnight. It was then filtered and concentrated to dryness under high vacuum at 50° C. for 1.5 h. The resulting brown oil was dissolved in dichloromethane (150 ml) cooled to −78° C. and $TiCl_4$ (99.995% purity, 4 ml) was added via syringe.

The suspension was stirred 15 min at −78° C., then allowed to warm to rt over 15 min before being cooled again to −78° C. Allyltributyltin (17 ml) was then added and the reaction allowed to proceed for 1 h. The black solution was poured into 200 ml of ethyl acetate and washed first with a saturated solution of $NH_4Cl$ (2×150 ml), then with water and brine. The organic phase was dried and concentrated to give the crude product, which was purified by column chromatography (cyclohexane, then cyclohexanelethyl acetate 98/2) to give the title compound (10.4 g) as a colourless oil.

NMR ($CDCl_3$) δ(ppm) 7.57 (d, 1H), 6.49 (dd, 1H), 6.45 (dd, 1H), 5.79 (m, 1H), 5.25 (dd, 1H) 5.24 (dd, 1H), 4.83 (d, 1H), 4.25 (q,2H), 4.13 (m, 1H), 2.66 (m, 2H), 1.30 (t, 3H).

Intermediate 2

(+)-Ethyl 2-(5-chloro-2-iodoanilino)-4-oxobutanoate

A solution of intermediate 1 (5.2 g) in dichloromethane (150 ml) was cooled to −78° C. and ozone was bubbled through it until the clear solution became brick-red. At this point the flux of ozone was interrupted and the solution was purged with nitrogen for a few minutes. Triphenyl phosphine (7.1 g) was added and stirring continued for 1.5 h, without control of the temperature. The resulting solution was poured into 200 ml of ethyl acetate and washed first with a saturated solution of $NH_4Cl$ (2×150 ml), then with water and brine. The organic phase was dried and concentrated to give the crude product, which was purified by column chromatography (cyclohexanelethyl acetate 80/20) to give the title compound (2.4 g) as a colourless oil.

NMR (DMSO) δ(ppm) 9.80 (t, 1H), 7.57 (d, 1H), 6.55 (d, 1H), 6.51 (dd, 1H), 4.99 (d, 1H), 4.46 (m, 1H), 4.24 (q, 2H), 3.08 (m, 2H), 1.28 (t, 3H)

Intermediate 2a (±) Ethyl 2-(3,5-dichloro-2-iodoanilino)-4-oxobutanoate

A solution of ethyl glyoxylate (50% solution in toluene, 1 ml) and $MgSO_4$ (7 g) in toluene (30 ml) was refluxed in Dean-Stark apparatus for 0.5 hrs.

Then, 3,5,-chloro-2iodoaniline was added, and the mixture refluxed for 1 hr. Then mixture was cooled, filtered througt celite to eliminate the MgSO4, and concentrated. The resulting brown oil was dissolved in dichloromethane (15 ml) cooled to −78° C. and $Yb(OTf)_3xH_2O$ (0.186 g) was added. The suspension was stirred for 5 mins at −78° C., then the vinyloxytrimethylsilane (0.29 g) was added and the temperature was risen to 20° C. After 1 hr at that temperature a saturated solution of NH4Cl (20 cc) was added followed by ethyl acetate (30 ml). The organic phase was washed with brine (20 ml) and dried over sodium sulphate and concentrated to give the crude product, which was purified by column chromatography (cyclohexane, then cyclohexane/ ethyl acetate 85/15) to give the title compound (0.562 g) as a colourless oil.

NMR ($CDCl_3$) δ(ppm) 9.65 (s, 1H), 7.00 (d, 1H), 6.70 (d, 1H), 5.60 (d, 1H), 4.80 (m, 1H) 4.10 (q, 2H), 3.10 (m, 2H), 1.15 (t, 3H).

Intermediate 3

Tributyl (2-oxo-1-phenylpyrrolidin-1-yl)phosphonium bromide

N,N N'N'-Tetramethylethylene diamine (23.3 ml) was added to a solution of N-phenylpyrrolidinone (5 g) in dichloromethane (50 ml). The solution was cooled to 0–5° and trmethylsilyl triflate (8.4 ml) was added over ca 20 mins maintaining the temperature in the range 0–5°. The resultant solution was stirred for 10 mins and a solution of pyridinium bromide perbromide (13 g) in acetonitrile (20 ml) was added over ca 20 mins maintaining the temperature in the range 0–10°. The resultant suspension was stirred at 0–5° for ca 60 mins. Aqueous sodium bicarbonate solution (50 ml) was added, cautiously. The mixture was stirred for ca 5 mins and the layers are separated. The aqueous phase was diluted with water (20 ml) and back extracted with dichloromethane (20 ml). The combined organic phases were washed with further sodium bicarbonate solution (50 ml), 2M hydrochloric acid (2×50 ml) and water (50 ml), back extracting each wash with dichloromethane (10 ml). The organic solution was dried ($MgSO_4$) and concentrated on a rotavapor. The red/brown solid was stirred with ethyl acetate (50 ml) and warmed to give a solution which was then cooled and tributylphosphine (8.5 ml) was added. The solution was heated to reflux and maintained at reflux for 2.5 hours. The solution was allowed to cool to room temperature and was then cooled to 0–5°. The resulting suspension was aged at 0–5° for ca 60 min. The product was isolated by vacuum filtration and then washed with ethyl acetate:t-butylmethylether (1:1, 40 ml) and dried in a vacuum oven at 45° to give the title compound as a white crystalline solid (10.12 g), mp 127–128°.

Intermediate 4

(±) E-Ethyl 2-(5-chloro-2-iodoanilino)-4-(2oxo-1-phenyl-3-pyrrolidinylidene) butanoate (4a);(1)-Z-Ethyl 2(5-chloro-2-iodoanilino)-4-(2-oxo-4-phenyl-3-pyrrolidinylidene) butanoate(4b)

To a solution of intermediate 2 (2.4 g) in acetonitrile (100 ml) at r.t. intermediate 3(3.7 g) and DBU (13 ml) were added and stirring was continued overnight at −20° C. The crude solution was poured into 200 ml of ethyl acetate and washed with a saturated solution of $NH_4Cl$ (2×150 ml), then with water and brine. The organic phase was dried and concentrated to give the crude product as a 4/1 mixture of 4a/4b compounds. Purification by column chromatography (cyclohexane/ethyl acetate 80/20) gave the title 4a (2.16 g) and the 4b (0.5 g) compounds as colourless oils.

Intermediate 4a

NMR ($CDCl_3$) δ(ppm) 7.72 (d, 2H), 7.56 (d, 1H), 7.38 (t, 2H), 7.16 (t, 1H), 6.6 (m, 1H), 6.50 (dd, 1H), 6.49 (d, 1H), 4.88 (d, 1H), 4.26 (m, 3H), 3.87 (t, 2H), 2.79 (m, 4H), 1.30 (t, 3H)

Intermediate 4b

NMR ($CDCl_3$) δ(ppm) 7.69 (d, 2H), 7.52 (d, 1H), 7.38 (t, 2H), 7.17 (t, 1H), 6.47 (d, 1H), 6.44 (dd, 1H), 5.98 (m, 1H), 5.00 (d, 1H), 4.22 (m, 2H), 4.13 (m, 1H), 3.84 (t, 2H), 3.2–3.6 (m, 2H), 2.85 (m, 2H), 1.26 (t, 3H)

Intermediate 5

(1R)-2-(tert-butoxy)-1-methyl-2-oxoethyl-2-(5-chloro-2-iodoanilino)-4-pentenoate (5a) and (1R)-2-(tert-butoxy)-4ethyl-2-oxoethyl-2-4-chloro-2-iodoanilino)-4-pentenoate (6b)

A solution of intermediate 1tert-butyl-(R)-2(oxoacetoxy)-2-methyl acetate (4.1 g) in toluene (200 ml) was refluxed in a Dean-Stark apparatus for 2 hrs. After cooling to room temperature, 5-chloro-2-iodoaniline (4.3 g) was added, and the solution refluxed in the presence of $MgSO_4$ for 3 hrs. The clear solution was cooled, filtered through cotton to eliminate the $MgSO_4$, concentrated to dryness and re-dissolved in dichloromethane (150 ml). The solution was cooled to −78° C., and $TiCl_4$ (1.9 ml) was added slowly from a syringe. After 15 min, allyl tributyltn (7.9 ml) was added, and the resulting black suspension was stirred for 1 hr. It was then poured onto ethyl acetate (300 ml), and saturated $NH_4Cl$ (150 ml) was added. The organic phase was separated, washed with water and brine, dried and concentrated. Final purification by column chromatography (cyclohexanefethyl acetate 95/5) afforded the title compound (4.1 g) (65/35 mixture of diastereomers) as a colourless oil (7.01 g).

NMR ($CDCl_3$) δ(ppm) 7.54 (1H), 6.46 (dd, 1H), 5.86 (m, 1H, 5.3–5.2 (m, 2H), 5.03 (m, 1H), 4.77 (bd, 1H), 4.16 (m, 1H), 2.8–2.68 (m, 2H), 1.50 (d, 3H), 1.45 (s, 9H)

Intermediate 5a (1R)-2-(ter-butoxy)-1-methyl-2-oxoethyl-2-(5-chloro-2-iodoanilino)-4-pentenoate To a solution of allyltributyl tin (3.3 g) in dry DCM (100 ml) a 1M solution in DCM of SnCl4 (10 ml) was added at −78 C. The mixture was stirred for 20 min, then intermediate 2-[2-(5-Chloro-2-iodo-phenylimino)-acetoxy]-1-(R)-methyl-acetic acid terbutyl ester (2.39 g) in dry DCM (50 ml) was added. The reaction was allowed to react at −78 C. for 20 min, then a saturated solution of NH4Cl was added and the resulting mixture was extracted with ethyl acetate (2×200 ml). The organic layer was washed with a solution of KF 10% in water, then diethyl ether was added and the resulting solid was filtered.

The solution was dried and evaporated under vacuum. Final purification by flash chromatography (CH/EA 95:5) give the title compound as pure diastereomer as a colourless oil (1.3 g).

NMR (CDCl3): 7.55 (d, 1H); 6.47 (d, 1H); 6.43 (d, 1H); 5.88 (m, 1H); 5.27 (m, 2H); 5.05 (q, 1H); 4.78 (d, 1H); 4.18 (m, 1HO; 2.74 (m, 2H); 1.52 (d, 3H); 1.67 (s, 9H).

IR (CDCl3): 3379, 1740

Intermediate 6

(1R)-2-(tert-butoxy)-1-methyl-2-oxoethyl-2-(5-chloro-2-iodoanilino)-4-oxobutanoate (6a) and (1R)-2(tert-butoxy)-1-methyl-2oxoethyl-2-(5-chloro-2-iodoanilino)-4-oxobutanoate (6b)

A solution of intermediate 5 (7.1 g) in dichloromethane (200 ml) was cooled to −78° C. and ozone was bubbled through it until the solution turned red. Triphenylphosphine (8 g) was then added, and the reaction allowed to stir for 2 hrs, without control of the temperature. The crude mixture was evaporated to dryness and purified repeatedly by column chromatography ((cyclohexanelethyl acetate 85/15) to afford the title compound 6a (2.75 g) and 6b(0.87 g) as colourless oils.

Compound 6a

NMR (CDCl$_3$) δ(ppm) 9.85 (t, 1H), 7.57 (d, 1H), 6.58 (d, 1H), 6.51 (dd, 1H), 5.04 (q, 1H), 4.96 (d, 1H), 4.62 (m, 1H), 3.13 (dd, 2H), 1.55–1.42 (m, 12H)

IR (CDCl3) (cm$^{-1}$) 1740

Compound 6b

NMR (CDCl$_3$) δ(ppm) 9.81 (t, 1H), 7.57 (d, $_1$H), 6.60 (d,1H), 6.52 (dd, 1H), 5.02 (q, 1H), 4.95 (d, 1H), 4.55 (m, 1H), 3.11 (m, 2H), 1.55–1.43 (m, 12H).

IR (CDCl3) (cm$^{-1}$) 1740

Intermediate 6a (1R)-2-(tert-butoxy)-1-methyl-2-oxoethyl-2-(5-chloro-2-iodoanilino)4-oxobutanoate The title compound was obtained starting from intermediate 5a following the same procedure described for intermediate 6.

Intermediate 7

(E)-(1R)-2-(tert-butoxy)-1-methyl-2oxoethyl 2-(5chloro-2-iodoanilino)-4-(2-oxo-1-phenyl-3-pyrrolidinylidene) butanoate (diastereoisomer A)

To a solution of intermediate 6a (2.7 g) in acetonitrile (60 ml) 2b(3 g) and DBU (1 ml) were added and the mixture was reacted at −20° C. overnight. It was then taken up with ethyl acetate (300 ml) and washed with 1N HCl, water and brine, dried and concentrated. Final purification by column chromatography (cyclohexane/ethyl acetate 85/15) afforded the title compound (2.1 g) as a white solid.

m.p. 36–39°, [α]$_D$ 22° (c=0.160% w/v in DMSO)

NMR (CDCl$_3$) δ(ppm) 7.72 (d, 2H), 7.55 (d, 1H), 7.38 (t, 2H), 7.15 (t, 1H), 6.66 (m, 1H, 6.49 (dd, 1H), 6.48 (d, 1H), 5.05 (m, 1H, 4.81 (d, 1H), 4.30 (m, 1H), 3.87 (t, 2H), 3.0 (m, 2H), 2.75 (m, 2H), 1.51 (d, 3H), 1.45 (s, 9H).

Intermediate 8

(−)-(1R)-2-tert-butoxy-1-methyl-2-oxoethyl 7-chloro-4-(1-phenyl-Δ$^3$-pyrrolin-2-one-3yl)-1,2,3,4-tetrahydroquinoline-2-carboxylate (8a)

(−)7-chloro-4-(2-oxo-1-phenyl-3-pyrrolidinylidene)-1,2,3,4-tetrahydro-2-quinoline2-carboxylic acid, [1-(R)-(1-tert-butoxycarbonyl)]ethyl ester (8b)

To a solution of intermediate 7 (2.1 g) in DMF (40 ml) Pd(PPh$_3$)$_4$ (0.393 g) and triethylamine (0.95 ml) were added and the mixture was heated to 150° C. for 1 hr. The crude solution was taken up with ethyl acetate and washed with 1N HCl, water and brine, dried and evaporated. Final purification by column chromatography (cyclohexane/dichloromethanelethyl acetate 50/40/10) afforded the title compound 8a (0.7 g) as a white solid.

m.p.=69–73° C.

[α]$_D$−70.1° (c=0.190% w/v in DMSO)

NMR (DMSO) δ(ppm) 7.80 (m, 2H), 7.39 (m, 2H), 7.12 (m, 1H), 6.82 (d, 1H), 6.77 (d, 1H), 6.70 (m, 1H), 6.49 (dd, 1H), 6.46 (bs, 1H), 4.93 (q, 1H), 4.49 (m, 2H), 4.02 (m, 1H), 3.87 (m, 1H), 2.44 (m, 1H), 2.00 (m, 1H), 1.39 (s, 9H), 1.38 (d, 3H).

IR (Nujol) (cm$^{-1}$) 3380, 1741, 1681, 1601 and the title compound 8b (0.8 g) as a yellow solid.

m.p.=59–64° C.

[α]$_D$−76.2° (c=0.510% w/v in DMSO)

NMR (DMSO) δ(ppm) 7.73 (m, 2H), 7.36 (m, 2H), 7.21 (d, 1H), 7.11 (m, 1H), 6.98 (da,1H), 6.75 (d, 1H), 6.57 (dd, 1H), 4.70 (q, 1H), 4.24 (m, 2H), 3.84 (m, 1H), 3.75 (m, 1H), 3.18 (m, 1H), 3.05 (m, 1H), 2.94 (m, 1H), 1.25 (s, 9H), 1.23 (d, 3H)

Intermediate 9

(±)-E-Ethyl 2-(5-chloro-2-iodoanilino)4-(2oxo-1-phenyl piperidinylidene) butanoate To a solution of tributyl-3-(1-phenyl-2-piperidinone) phosphonium bromide (0.83 g) in acetonitrile (20 ml) DBU (0.27 ml) was added and after 15 min a solution of the intermediate 2 (0.35 g) in acetonitrile (20 ml). The reaction mixture was stirred for 30 min, then diluted with ethyl acetate and washed with a 1N solution of HCl and brine. The organic phase was dried and concentrated to give the crude product which was purified by flash column chromatography to obtain the title compound (0.29 g) as pale yellow foam.

NMR (CDCl$_3$) δ(ppm) 7.56 (dd, 1H), 7.38 (dd, 2H), 7.27 (dd, 2H), 7.24 (t, 1H), 6.93 (t, 1H), 6.50–6.47 (m, 2H), 4.85 (d, 1H), 4.25 (q, 2H), 4.22 (m, 1H), 3.71 (m, 2H), 2.76, (m, 2H), 2.59 (m, 2H), 2.01 (m, 2H), 1.29 (t, 3H)

Intermediate 10

(±)-Ethyl 2-(5-chloro-2-iodoanilino)-4-(2-oxo-1-(pyridin-3-yl)-pyrrolidin-3-ylidene)butanoate To a solution of the (1-(pyridin-3-yl)-2-oxo-pyrrolidin-3-yl)tributylphosphonium bromide (0.93 g) in acetonitrile (10 ml) DBU (0.22 ml) was added and after 10 min a solution of the intermediate 2 (0.46 g) in acetonitrile (10 ml). The reaction mixture was stirred for 3 hr. then diluted with ethyl acetate and washed with a saturated solution of NH$_4$Cl and brine. The organic phase was dried and concentrated to give the crude product which was purified by flash column chromatography to obtain the title compound (0.47 g) as a mixture of E/Z isomer (80/20).

MS (m/z) 526

Intermediate 11

(±)-E-Ethyl 2-(3,5-dichloro-2-iodoanilino)-4-(2-oxo-1-phenyl-3-pyrrolidinylidene)butanoate (11a);(±)-Z-Ethyl 2-(3,5-dichloro-2-iodoanilino)-4-(2-oxo-1-phenyl-3-pyrrolidinylidene)butanoate (11b)

To a solution of intermediate 2a in acetonitrile (10 ml) at r.t 2b (0.726 g) and DBU (0.33 ml) were added and stirring was continued overnight at −20° C. The crude solution was poured into 20 ml of ethyl acetate and washed first with a saturated solution of NH$_4$Cl (2×15 ml), then with water and brine. The organic phase was dried and concentrated to give the crude product as a 4/1 mixture of Z/E isomers. Purification by column chromatography (cyclohexanelethyl acetate 85/15) gave the title compound 11a (0.498 g) and the title compound 11b (0.122 g) as colourless oils.

intermediate 11a

NMR (CDCl$_3$) δ(ppm) 7.78 (d, 2H), 7.39 (t, 2H), 7.16 (t, 1H), 6.90 (d, 1H), 6.58 (m, 1H), 6.36 (d, 1H), 5.22 (d, 1H), 4.26 (m, 3H), 3.87 (t, 2H), 2.79 (m, 4H), 1.30 (t, 3H)

IR (CDCl$_3$) (cm$^{-1}$) 3370, 1738, 1697, 1671.

MS (m/z) 559.

intermediate 11b

NMR (CDCl$_3$) δ(ppm) 7.69 (d, 2H), 7.38 (t. 2H), 7.17 (t, 1H), 6.84 (d, 1H), 6.34 (d, 1H), 5.96 (m, 1H), 5.34 (d, 1H), 4.22 (m, 2H), 4.12 (m, 1H), 3.84 (t, 2H), 3.63–3.27 (m, 2H), 2.85 (t, 2H), 1.26 (t, 3H)

IR (CDCl3) (cm$^{-1}$) 1733, 1685.

MS (m/z) 559.

Intermediate 12

-(1R)-2-(tert-butoxy)-1-methyl-2-oxoethyl 2-(5-chloro-2-iodoanilino)-4-(2oxo-1-phenyl-3-pyrrolidinylidene) butanoate (diastereoisomer To a solution of intermediate 6b (0.87 g) in acetonitrile (20 ml) tributyl-3-(N-phenyl-1-pyrrolidonyl)phosphonium bromide (1.6 g) and DBU (0.33 ml) were added and the mixture was reacted at −20° C. overnight. It was then taken up with ethyl acetate (100 ml) and washed with 1N HCl, water and brine, dried and concentrated. Final purification by column chromatography (cyclohexanelethyl acetate 85/15) afforded the title compound (0.47 g) as a white solid oil.

m.p.=38–42° C.

NMR (CDCl$_3$) δ(ppm) 7.72 (d, 2H), 7.55 (d, 1H), 7.38 (t, 2H), 7.16 (t, 1H), 6.60 (m, 1H), 6.56 (d, 1H), 6.49 (dd, 1H). 5.03 (q, 1H), 4.80 (d, 1H), 4.33 (m, 1H), 3.88 (t, 2H), 2.9 (m, 2H), 2.75 (m, 2H), 1.48 (d, 3H), 1.44 (s, 9H).

IR (CDCl$_3$) (cm$^{-1}$) 3375, 1738, 1693, 1665

Intermediate 13

-(1R)-2-(tert-butoxy)-1-methyl-2-oxoethyl 7-chloro-4-(1-phenyl-Δ$^3$-pyrrolin-2-one-3yl)-1,2,3,4-tetrahydroquinoline-2-carboxylate (diastereoisomer B)

To a solution of intermediate 12 (0.46 g) in DMF (8 ml) Pd(PPh$_3$)$_4$ (0.043 g) and triethylamine (0.21 ml) were added and the mixture was heated to 150° C. for 1 hr. The crude solution was taken up with ethyl acetate and washed with 1N HCl, water and brine, dried and evaporated. Final purification by column chromatography (cyclohexane/dichloromethane/ethyl acetate 50/40/10) afforded the title compound (0.114 g) as a white solid.

m.p.=62–67° C.

NMR (DMSO) δ(ppm) 7.79 (m, 2H). 7.38 (m, 2H), 7.11 (t, 1H), 6.81 (d, 1H), 6.77 (d, 1H), 6.70 (d, 1H), 6.55 (bs, 1H), 6.48 (dd, 1H), 4.90 (q, 1H), 4.5 (m, 2H), 3.99 (m, 1H), 3.84 (t, 1H), 2.35 (m, 1H), 2.02 (m, 1H), 1.39 (s, 12H).

Intermediate 14

2,4dibromo-N-(4-(tert-butoxycarbonylamino)phenyl)-butyramide

To the derivative 2,4- dibromobutyryl bromide (3.1 g) in dry dichloromethane (60 ml) pyridine (3.2 ml) was added, the mixture was kept at 0° C. under a nitrogen atmosphere for 10 minutes and then the N-t-butoxy carbonyl-1,4 phenylene diamine (2.08 g) was dropped. After 1 hour the mixture was poured into a saturated solution of NH$_4$Cl (200 ml) extracted with EA (3×150 ml) and the organic phase washed with brine (200 ml), dried and concentrated in vacuum, the crude was purified by flash chromatography (eluting with CH/EA 80:20) to give of the title compound as a yellow foam (3.5 g ). T.l.c. CH/EA 8:2, R$_f$=0.53.

$^1$H-NMR: 7.89 (sa); 7.44 (d); 7.35 (d); 6.46 (sa); 4.66 (dd); 3.60 (m); 2.76(m); 2.55(m); 1.51(s).

Intermediate 15

3-bromo-1-(4-(tert-butoxycarbonylamino)phenyl-2-oxo-pyrrolidine

To a solution of intermediate 14 (3.5 g) in dry THF (50 ml) cooled (0° C.), a solution of LHMDS (9.6 ml of a 1M solution in tetrahydrofuran) was added drop-wise. The mixture was stirred under nitrogen until the temperature reached r.t for 2 hours. Then it was quenched into a saturated solution of NH$_4$Cl (200 ml) extracted with EA (3×150 ml) and the organic extracts were washed with brine (200 ml), dried and concentrated in vacuum. The mixture was purified by flash chromatography (eluting with CH/EA 8:2) to give the title compound (2.6 g). T.l.c. CHIEA 8:2, R$_f$=0.31. $^1$H-NMR: 7.57 (d); 7.39 (d); 6.49 (sa); 4.59 (m); 4.03 (m); 3.81 (m); 2.73 (m); 2.46 (m); 1.53(s).

Intermediate 16

(+/−)-Z-Ethyl2-(5chloro-2-iodoanilino)-4-(2-oxo-1-(4-tert-butoxycarbonylamino)phenyl-pyrrolidin-3-ylidene) butanoate A solution of intermediate 15 (2.6 g) in dry DMF (100 ml) and tributylphosphine was refluxed at 110° C. under a nitrogen atmosphere for 4 h, until reaction completion (TLC). The mixture was concentrated in vacuum to give the crude1-(4-tert-butoxycarbonylamino)phenyl-2-oxo-pyrrolidin-3-yl-tributylphosphonium bromide (1.75 g) which was dissolved in dry CH$_3$CN (100 ml) was cooled at −30° C. and stirred under a nitrogen atmosphere, then DBU (0.44 ml) and intermediate 2 (1.0 g) were added. The mixture was stirred for 1 h then was poured into a saturated solution of NH$_4$Cl (200 ml) extracted with EA (3×150 ml) and the organic extracts were washed with brine (200 ml), dried and concentrated in vacuum to give a yellow oil which was purified by flash chromatography (eluting with CH/EA 80:20) to give the title compound (0.085 g) as a white solid.

T.l.c. CH-EA (7:3), R$_f$=0.23 IR: 1727 and 1695 (C=O) cm$^{-1}$. $^1$H-NMR: 7.64 (d); 7.53 (d); 7.38 (d); 6.48 (d); 6.47 (sa); 6.45 (dd); 5.97(m); 5.02(d); 4.23 (m); 4.14 (m); 3.8(t); 3.6 (m); 3.3 (m); 2.85 (m); 1.53(s); 1.27(t).

Intermediate 17

(±)-Z-Benzyl 2-(5-chloro-2-iodoanilino)-4-(2,5-dioxo-1-phenyl-imidazolidinylidene)butanoate To a solution of the derivative N-(phenylaminocarbonyl) α-phosphonoglycine-trimethyl ester (0.1 g) in acetonitrile (10 ml) DBU (0.1 ml) was added and after 10 min a solution of the (+/−)-2-(5-Chloro-2-iodo-phenylamino)-4-axo-butyric acid benzyl ester (0.1 g) in acetonitrile (2 ml). The reaction mixture was stirred for 1½ hr, then diluted with ethyl acetate and washed with a 1N solution of HCl and brine. The organic phase was dried and concentrated to give the crude product which was purified by flash column chromatography to obtain the title compound (0.065 g)

NMR (DMSO) δ(ppm) 10.80 (s, 1H), 7.65 (d, 1H), 7.7–7.3 (m, 10H), 6.75 (d, 1H), 6.55 (dd, 1H), 5.70 (t, 1H), 5.20 (s, 2H), 5.07 (d, 1H), 4.72 (m, 1H, 2.86 (t, 2H IR (Nujol) (cm$^{-1}$) 3339, 3160, 1768, 1721, 1691

Intermediate 18

(±)-Benzyl 7chloro-4-(2,5-dioxo-1-phenyl-imidazolidin-4-ylidene)-1,2,3,4-tetrahydro-2-quinolinecarboxylate To a solution of intermediate 17 (0.065 g) in DMF (5 ml) Pd(PPh$_3$)$_4$ (16 mg) and TEA (0.05 ml) were added and the resulting solution was heated to 110° C. for 1 h. The crude solution was poured into ethyl acetate and washed with a 1N solution of HCl and brine. The organic phase was dried and concentrated to give the crude product which was purified by flash column chromatography to obtain the title compound (0.015 g) as yellow powder.

m.p.>220° C.

NMR (DMSO) δ(ppm) 10.5 (s, 1H), 7.5–7.2 (m, 11H), 7.16 (bd, 1H), 6.75 (d, 1H, 6.58 (dd, 1H, 5.2–5.01 (dd, 2H), 4.40 (m, 1H), 4.25 (dd, 1H), 2.83 (dd, 1H).

IR (Nujol) (cm$^{-1}$) 3378, 1752, 1728, 1704

Intermediate 19

2-[2-(5-chloro-2-iodo-phenylimino)-acetoxy]-1-(R)-methyl-acetic acid isobutyl ester To a solution of acrylic acid 1-isobutoxycarbonyl-1R)-methyl-methyl ester (3.7 g) in THF/H$_2$O OsO4 4% in H$_2$O (4 ml) was added. The black suspension was then treated with NaIO4 (10.5 g) by portions. After 5 hrs, the solution was taken up with ethyl acetate (2×50 ml) and washed with water (2×50 ml). The organic phase evaporated under vacuum and the crude mixture was purified by flash chromatography (CH/EA 1:1) to afford 2-(2-Oxo-acetoxy)-1-(R)-methyl-acetic acid isobutyl ester as colourless oil (3 g). 24.8 g of 2-(2-Oxo-acetoxy)-1-(R)-methyl-acetic acid isobutyl ester was dissolved in toluene (1000 ml) and refluxed in a Dean-Stark apparatus for 2 hrs. After cooling to room temperature, 5chloro-2-iodoaniline (22 g) was added, and the solution refluxed in the presence of $MgSO_4$ for 3 hrs. The clear solution was cooled, filtered through cotton to eliminate the $MgSO_4$, concentrated to dryness to obtain the title compound (38 g) as a yellow oil.

NMR ($CDCl_3$) δ(ppm) 7.83 (1H, d), 7.79 (s 1H), 7.02 (dd,1H),6.96 (d, 1H), 5.373 (q 1H), 4.00 (m, 2H), 2.00 (m, 1H), 1.67 (d, 3H), 0.96 (2d, 6H)

IR (CDCl3): 1749, 1730

Intermediate 20

2-(5Chloro-2-iodo-phenylamino)-4-oxo-butyric acid 1-isobutoxycarbonyl-1(R)-methyl-methyl ester (20a and 20b)

A solution of intermediate 19 (38 g) in toluene (1 ml) was cooled to −20° C. and Yb(OTf)3 (16.5 g) was added and, after a few minutes, vinyloxy trimethylsilane (12.5 g) dissolved in toluene (50 ml) was added drop-wise. The bath was removed and the reaction allowed to stir for 2 hrs. The crude mixture was taken up with ethyl acetate (500 ml) and the organic phase was washed with a saturated solution of ammonium chloride (300 ml) and evaporated. Then, the mixture was purified by column chromatography (cyclohexane/ethyl acetate 85/15) to afford the title compounds 20a (14 g) and 20b (4 g) as colourless oils.

Intermediate 20a

NMR ($CDCl_3$) δ(ppm) 9.85 (s, 1H), 7.57 (d, 1H), 6.58 (d, 1H), 6.51 (dd, 1H), 5.19 (m, 1H), 4.97 (d, 1H), 4.63 (m, 1H), 3.93 (m, 2H), 3.24–3.04 (m, 2H, 1.94 (m, 1H), 1.53 (d, 3H), 0.93 (dt, 3H); 0.91 (d, 3H).

IR (CDCl3) ($cm^{-1}$) 1742, 1740

Intermediate 20b

NMR ($CDCl_3$) δ(ppm) 9.81 (s, 1H), 7.57 (d, 1H), 6.60 (d,1H, 6.52 (dd, 1H), 5.17 (m, 1H), 4.95 (d, 1H), 4.57 (m, 1H, 3.92 (m, 2H), 3.11 (m, 2H); 1.92 (m, 1H); 1.50 (d, 3H); 0.90 (d, 6H).

IR (CDCl3) ($cm^{-1}$) 3375, 1734

Intermediate 21

(E)-2-(5-Chloro-2-iodo-phenyl-pyrrolidin-3-ylidene)-butyric acid 1-isobutoxycarbonyl-1-(R) methyl-methyl ester To a solution of intermediate 3 (14.45 g) in acetonitrile (200 ml) DBU (4.43 ml) was added at room temperature and the mixture was stirred for 10 min. The mixture was then cooled at −25° C. and intermediate 31a (12.98 g) in 60 ml of CH3CN was added drop-wise in 15 min. Then the reaction was stirred at this temperature for 2 h. Then the mixture was taken up with ethyl acetate (100 ml) and the organic phase washed with a saturated solution of NH4Cl (150 ml), and HCl 2% (200 ml) and brine (2×200 ml). The solution was then dried and concentrated. Final purification by column chromatography (cyclohexane/ethyl acetate/ CH2Cl2 7/0.5/2.5) afforded the title compound (11.04 g) as a white foam.

NMR ($CDCl_3$) δ(ppm) 7.73 (m, 2H), 7.56 (d, 1H), 7.38 (t, 2H), 7.16 (m, 1H), 6.67 (m, 1H), 6.50(dd, 1H), 6.49 (s, 1H), 5.20 (q, 1H, 4.81 (d, 1H), 4.33 (m, 1H), 3.94 (d, 2H), 3.88 (t, 2H), 3.0–2.74 (m, 4H), 1.94 (m, 1H), 1.57 (d, 3H); 0.91 (d, 6H).

IR (CDCl3); 1696, 1670cm−1

Intermediate 22

7-Chloro-4-(2-oxo-1-phenyl-pyrrolidin-3-ylidene)-1,2,3,4-tetrahydro-quinoline-2-carboxylic acid, [1-(R)-methyl-1-isobutoxcarbonyo-methyl ester (diastereolsomer A)

To a solution of intermediate 21 (9.55 g) in toluene (130 ml), $Pd(PPh_3)_4$ (3.52 g) and triethylamine (5.1 ml) were added in portions and the mixture was heated to 110° C. for 3.5 hr. The crude solution was taken up with ethyl acetate (600 ml) and washed with NH4Cl and brine, dried and evaporated. Purification by column chromatography (cyclohexane/dichloromethane/ethyl acetate 6.5/3/0.5) afforded the title compound (6.08 g) as a yellow foam.

NMR (DMSO) δ(ppm) 7.71 (d, 2H), 7.35 (t, 2H), 7.20 (d, 1H), 7.11 (t, 1H), 7.00 (s,1H), 6.74 (d, 1H), 6.57 (dd, 1H, 4.89 (q, 1H), 4.24 (m, 2H), 3.84–3.60 (m, 4H), 3.2–2.8 (m, 3H), 1.70 (m, 1H), 1.24 (d, 3H); 0.73 (d, 6H).

IR (nujol): 3377, 1746, 1670

Intermediate 23

7Chloro-4-(2-oxo-1-phenyl-2,5-dihydro-1H-pyrrol-3-yl)-1,2,3,4-tetrahydroquinoline-2-carboxylic acid, [1-(R)-methyl-1-isobutoxycarbonyl]-methyl ester To a solution of intermediate 22 (3.67 g) in DMF (50m1) $Pd(PPh_3)_4$ (0.340 g) and triethylamine (2 ml) were added and the mixture was heated to 110° C. for 2 hrs. The crude solution was taken up with ethyl acetate (2×200 ml) and washed with NH4Cl and brine, dried and evaporated. Final purification by column chromatography (cyclohexane/ dichloromethane/ethyl acetate 6.5/3/0.5) afforded the title compound (1.289 g) as a yellow foam.

NMR (DMSO) δ(ppm) 7.79 (d, 2H), 7.38(t, 2H), 7.11 (t, 1H), 6.79 (d, 1H), 6.57 (d, 1H), 6.74 (d, 1H); 6.47 (dd, 1H); 6.47 (m, 1H); 5.10 (q, 1H); 4.49 (m, 2H); 4.06 (m, 1H); 3.92–3.82 (m, 3H); 2.45 (m, 1H); 2.019 (m, 1H); 1.84 (m, 1H); 1.42 (d, 3H); 0.84 (d, 6H).

IR (nujol): 3375, 1749,1683.

Intermediate 24

2(3,6-Dichloro-2-iodo-phenylamino)-4-oxo-butyric acid 1-n-butoxycarbonyl-1-(S)-methyl-methyl ester (24a and 24b)

To a solution of intermediate Acrylic acid 1-n-butoxycarbonyl-1-(S)-methyl-methyl ester(4.9 g) in THF/ $H_2O$ (100 ml, 2/1) OsO4 4% in $H_2O$ (2.8 g) was added. The black suspension was then treated with NaIO4 (13 g) by portions. After 5 hrs, the solution was taken up with ethyl acetate (2×50 ml) and washed with water (2×50 ml). The organic phase evaporated under vacuum and the crude mixture was purified by flash chromatography (CH/EA 1:1) to afford the 2-(2-oxo-acetoxy)-1-(S)-methyl-acetic acid n-butyl ester as a colourless oil (4.85 g). (2.5 g) of which was dissolved in toluene (200 ml) and refluxed in a Dean-Stark apparatus for 2 hrs. After cooling to room temperature, 3,5-dichloro-2-iodoaniline (2.46 g) was added, and the solution refluxed in the presence of $MgSO_4$ for 3 hrs. The clear solution was cooled, filtered through cotton to eliminate the $MgSO_4$, concentrated to dryness to obtain (2-(2-(5-chloro-2-iodo-phenylimino)acetoxy]-1-(S)-methyl-acetic acid n butyl ester(4 g,) as a yellow oil.

A solution of such a yellow oil in CH3CN (70 ml) was cooled to −30° C. and Yb(OTf)3 (2.1 g) was added and, after a few minutes, vinyloxy trimethylsilane (1.1 g) dissolved in CH3CN (20 ml) was added, drop-wise. The reaction was stirred for 10 min. The crude mixture was taken up with ethyl acetate (500 ml) and the organic phase was washed with a saturated solution of ammonium chloride (2×50 ml) and evaporated. Then, the mixture was purified by column chromatography (cyclohexane/ethyl acetate 90/10) to afford the title compounds 24a (1.4 g) and 24b (0.7 g) as colourless oils.

Intermediate 24a

NMR (CDCl$_3$) δ(ppm) 9.84 (t, 1H), 6.92 (d, 1H); 6.45 (d, 1H); 5.33 (da, 1H); 5.17 (q, 1H); 4.60 (m, 1H); 4.14 (m, 2H); 3.34–3.06 (m, 2H); 1.6 (m, 2H); 1.52 (d, 3H); 1.37 (m, 2H); 0.93 (t, 3H).

IR (CDCl3) (cm$^{-1}$) 3370,1742

Intermediate 24b

NMR (CDCl$_3$) δ(ppm) 9.80 (s, 1H), 6.92 (d, 1H); 6.47 (d, 1H); 5.3 (da, 1H); 5.15 (q, 1H); 4.55 (m, 1H); 4.14 (m, 2H); 3.13 (m, 2H); 1.57 (m, 2H); 1.49 (d, 3H); 1.34 (m, 2H); 0.91 (t, 3H).

IR (CDCl3) (cm$^{-1}$) 3370, 1744.

Intermediate 25

(E)-2-(3,5-Dichloro-2-iodo-phenylamino)-4-(2-oxo-1-phenyl-pyrrolidin-3-ylidene)-butyric acid 1-n-butoxycarbonyl-1-(S) methyl-methyl ester (diastereoisomerA)

To a solution of intermediate 2a (0.893) in acetonitrile (20 ml) DBU (0.25 ml) was added at room temperature and the mixture was stirred for 10 min. The mixture was then cooled at −25° C. and intermediate 6b (0.8 g) in 10 ml of CH3CN was added drop-wise in 15 min. Then the reaction was stirred at this temperature for 30 min. Then the mixture was taken up with ethyl acetate (50 ml) and the organic phase washed with a saturated solution of NH4Cl (50 ml), and HCl 2% (10 ml) and brine (2×20 ml). The solution was then dried and concentrated. Final purification by column chromatography (cyclohexanelethyl acetate 8/2) afforded the title product (0.734 g) as a white foam.

NMR (CDCl$_3$) δ(ppm) 7.72 (d, 2H), 7.39 (t, 2H), 7.17 (t, 1H); 6.92 (d, 1H); 6.60 (m, 1H); 6.43 (d, 1H); 5.16 (q, 1H); 5.14 (d, 1H); 4.34 (d, 1H); 4.15 (m, 2H); 3.89 (t, 2H); 2.75–2.4 (m, 4H); 1.60 (m, 2H); 1.53 (d, 3H); 1.34 (m, 2H); 0.91 (t, 3H).

IR (CDCl3); 3377,1744, 1697, 1672 cm−1

Intermediate 26

5,7-Dichloro-4-(2-oxo-1-phenyl-2,5-dihydro-1H-pyrrol-3-yl)-1,2,3,4-tetrahydroquinoline-2-carboxylic acid, [1-(S) methyl-1-n-butoxycarbonyl]-methyl ester (26a)5,7-Dichloro-4-(2-oxo-1-phenylpyrrolidin-3-ylidene)-1,2,3,4-tetrahydro-quinoline-2-carboxalic acid, [1(S)-methyl-1-n-butoxycarbonyl]methyl ester (26b)

To a solution of intermediate 25 (0.734 g) in DMF (20 ml) Pd(OAc)$_2$ (0.110 g) and triethylamine (0.37 ml) were added in portions, and the mixture was heated to 120° C. for 3 hr. The crude solution was taken up with ethyl acetate (100 ml) and washed with NH4Cl and brine, dried and evaporated. Final purification by column chromatography (cyclohexane/dichloromethanelethyl acetate 7/2.5/0.5) afforded the title compound 26 a (0.35 g) and 26b(0.06 g) as a yellow foam.

Intermediate 26a

NMR (DMSO) δ(ppm) 7.80(d, 2H); 7.38 (t, 2H); 7.11 (t, 1H); 6.89 (d, 1H); 6.83 (s, 1H); 6.68 (d, 1H); 6.47 (d, 1H); 5.07 (q, 1H); 4.48 (m, 2H); 4.11 (m, 1H); 4.06 (t, 2H); 3.8 (dd, 1H); 2.3–1.8 (m, 2H); 1.52 (m, 2H); 1.40 (d, 3H); 1.54 (m, 2H); 1.3 (m, 2H); 0.84 (t, 3H).

IR (nujol): 3374, 1740, 1683 cm$^{-1}$

Intermediate 26b

NMR (DMSO) δ(ppm) 7.69 (d, 2H); 7.39 (t, 2H); 7.33 (d, 1H); 7.15 (t, 1H); 6.71 (d, 1H); 6.62 (d, 1H); 4.72 (d, 1H); 4.40 (q, 1H); 4.40 (m, 1H); 3.94 (t, 2H); 3.76 (t, 1H); 3.60 (q, 1H); 3.12 (m, 1H; 2.35 (m, 1H); 2.21 (dd, 1H); 1.42 (m, 2H); 1.21 (m, 2H); 0.97 (d, 3H); 0.82 (t, 3H).

IR (nujol): 3377, 1746, 1684, 1594 cm$^{-1}$

EXAMPLE 1

(±)-Sodium 7-chloro-4-(1-phenyl-Δ$^3$-pyrrolin-2-one-3-yl)-1,2,3,4-tetrahydroquinoline-2-carboxylate To a solution of example 31a (540 mg) in IMS (5% methanol in absolute ethanol, 7 ml) NaOH (1N,1.4 ml) was added and stirring continued for 2 hrs. The resulting solution was dried on the rotary evaporator and the resulting solid was triturated with diethyl ether. After filtration and drying the title compound (440 mg) was obtained as an off-white solid.

m.p.>200° C.

NMR (DMSO) δ(ppm) 7.80 (m, 2H), 7.39 (m, 2H), 7.11 (m, 1H), 6.80 (d, 1H), 6.72 (d, 1H), 6.36 (d, 1H), 6.34 (dd, 1H), 5.71 (s, 1H), 4.42 (m, 2H), 3.77 (m, 1H), 3.13 (m, 1H), 2.29 (m, 1H), 1.44 (m, 1H).

IR (Nujol) (cm$^{-1}$) 1672, 1600.

EXAMPLE 2

(−)-Sodium 7-chloro-4-(1-phenyl-Δ$^3$-pyrrolin-2-one-3yl)-1,2,3,4-tetrahydroquinoline-2-carboxylate To a solution of intermediate 8a (690 mg) in THF/H$_2$O (1/1) (14 ml) LiOH (65 mg) was added and stirring continued for 1 h. The resulting solution was concentrated to dryness, taken up with ethyl acetate and 1N HCl was added. After vigorous stirring, the organic phase was separated, washed with water and brine and concentrated. The resulting solid was dissolved in THF (15 ml) and treated with sodium ethylhexanoate (232 mg) for 30 min. After drying, the resulting solid was triturated with hot diethyl ether and filtered, to afford the title compound (160 mg) as a white solid.

e.e.=99%

[α]$_D$=−102.3° (c=0.09% w/v in DMSO)

m.p.>200° C.

NMR (DMSO) δ(ppm) 7.80 (m, 2H), 7.39 (m, 2H), 7.11 (m,1H, 6.80 (d, 1H), 6.72 (d, 1H), 6.36 (d, 1H), 6.34 (dd,$_1$H, 5.71 (s, 1H), 4.42 (m, 2H), 3.77 (m, 1H), 3.13 (m, 1H), 2.29 (m, 1H), 1.44 (m, 1H).

IR (Nujol) (cm$^{-1}$) 1672, 1600.

EXAMPLE 3

(±)-Ethyl 7-chloro-4-(1-phenyl-Δ$^3$-5,6dihydro-2-pyridin-2-one-3yl-1,2,3,4-tetrahydroquinoline-2-carboxylate (3a)

(±)-Ethyl 7-chloro-4-(2-oxo-1-phenyl-3-piperidinylidene)1,2,3,4-tetrahydro-2-quinolinecarboxylate (3b)

To a solution of intermediate 9 (0.2 g) in DMF (5 ml) Pd(PPh$_3$)$_4$ (41 mg) and TEA (0.1 ml) were added and the resulting solution was heated to 110° C. for 2 hrs. The crude solution was poured into ethyl acetate and washed with a 1N solution of HCl and brine. The organic phase was dried and concentrated to give the crude product which was purified by flash column chromatography to obtain the title compound 3a (0.085 g) as a white powder.

m.p.=131–133° C.

NMR (DMSO) δ(ppm) 7.4–7.3 (m, 4H), 7.20 (t,$_1$H, 6.78 (d,$_1$H, 6.75 (d, 1H), 6.48 (dd, 1H), 6.34 (bs, 1H), 5.99 (t, 1H), 4.13 (m, 2H), 3.97 (t, 1H), 3.93 (dd, 1H), 3.77 (m, 2H), 2.45 (m, 2H), 2.15 (m, 1H), 1.85 (m, 1H), 1.19 (t, 3H).

IR (Nujol) (cm$^{-1}$) 3392, 1723, 1659 and the title compound 3b (0.055 g) as pale yellow powder.

m.p.=99–101° C.

NMR (DMSO) δ(ppm) 7.4–7.2 (m, 5H), 7.01 (d, 1H), 6.93 (d, 1H), 6.68 (d, 1H), 6.52 (dd, 1H), 4.20 (m, 1H), 4.16–3.96 (m, 2H), 3.74–3.60, 3.40 (m, 2H), 2.9–2.5 (m, 3H), 2.0–1.6 (m, 2H), 1.14 (t, 3H).

EXAMPLE 4

(±)-Ethyl 7chloro-4-(1-pyridin-Δ³-pyrrolin-2-one-3yl)-1,2,3,4-tetrahydroquinoline-2-carboxylate (4a)

(±)-Ethyl 7-chloro-4-(2-oxo-1-(pyridin3-yl)-pyrrolidin-3-ylidene)-1,2,3,4-tetrahydro-2-quinolinecarboxylate (4b)

To a solution of example 3 (0.47 g) in DMF (20 ml) Pd(PPh$_3$)$_4$ (100 mg) and TEA (0.38 ml) were added and the resulting solution was heated to 110° C. for 1½ h. The crude solution was poured into ethyl acetate and washed with a saturated solution of NH$_4$Cl and brine. The organic phase was dried and concentrated to give the crude mixture which was dissolved in ethyl acetate (2 ml) and treated with petroleum (2 ml) the solid was filtered to give the title compound 4a (0.08 g) as a white powder.

m.p.=132–134° C.

NMR (DMSO) δ(ppm) 8.99 (d, 1H), 8.32 (dd, 1H), 8.21 (m, 1H), 7.41 (dd, 1H), 6.80 (d, 1H), 6.77 (m, 1H), 6.75 (d, 1H), 6.47 (dd, 1H), 6.45 (m, 1H), 4.56 (m, 1H), 4.50 (m, 1H), 4.24.02 (m, 2H), 3.99 (m, 1H), 3.81 (t, 1H), 2.31 (m, 1H), 1.97 (m, 1H), 1.18 (t, 3H).

IR (Nujol) (cm$^{-1}$) 3391, 1728, 1679

The mother liquor was purified by flash chromatography to obtain a product which was triturated in cyclohexane to obtain title compound 4b (0.067 g, yellow powder).

NMR (DMSO) δ(ppm) 8.94 (d, 1H), 8.34 (dd, 1H), 8.14 (m, 1H), 7.41 (dd, 1H), 7.19 (d, 1H), 7.00 (d, 1H), 6.73 (d, 1H), 6.56 (dd, 1H), 4.27 (m, 1H), 4.20 (m, 1H), 4.00 (m, 1H), 3.89 (m, 1H), 3.85 (m, 1H), 3.72 (m, 1H). 3.21 (m, 1H), 2.93 (m, 1H), 2.84 (m, 1H), 0.90 (t, 3H).

IR (Nujol) (cm$^{-1}$) 3366, 1734, 1676.

EXAMPLE 5

(±)-Ethyl 5,7dichloro-4-(1-phenyl-Δ³-pyrrolin-2-one-3yl)-1,2,3,4-tetrahydroquinoline-2-carboxylate To a solution of intermediate 11 a (0.430 g) in DMF (10 ml) Pd(OAc)$_2$ (11.6 mg) and TEA (0.12 ml) were added and the resulting solution was heated to 130° C. for 2 h. The crude solution was poured into 20 ml of ethyl acetate and washed first with a saturated solution of NH$_4$Cl (2×15 ml), then with water and brine. The organic phase was dried with Na$_2$SO$_4$ and concentrated to give the crude product. Purification by column chromatography (cyclohexane/dichloromethane/ethyl acetate 60/30/10) gave the title compound (0.087 g) as an off-white solid.

NMR (DMSO) δ(ppm) 7.81 (m, 2H), 7.40 (m, 2H), 7.13 (m, 1H), 6.91 (d, 1H), 6.75 (Sa, 1H), 6.68 (d, 1H), 6.45 (m, 1H), 4.46 (m, 2H), 4.17–4.10 (m, 3H), 3.79 (dd, 1H), 2.31 (m, 1H), 1.84 (m, 1H), 1.20 (t, 3H)

IR (Nujol) (cm$^{-1}$) 3390, 1724,1678.

EXAMPLE 6

(+/-)-Ethyl 7-chloro-4-(1-(4-tert-butoxycarbonylamino)-phenyl-Δ³-pyrrolin-2-one-3-yl)-1,2,3,4-tetrahydroquinoline-2-carboxylate A solution of intermediate 16 (0.085 g) in dry DMF (5 ml) was stirred in the presence of TEA (0.018 ml) and Pd(OAc)$_2$ (0.0015 g) under a nitrogen atmosphere at 110° C. for 1 h. The mixture was diluted with a saturated aqueous ammonium chloride solution (100 ml) and EA (100 ml); the organic layer was washed with brine (100 ml), dried and concentrated in vacuum. The crude mixture was purified by flash chromatography (eluting with CH/EA 8:2) to give the title compound as a yellow solid (0.050 g).

T.l.c. CH-EA (8:2) R$_f$=0.30. ¹H-NMR:9.30 (sa); 7.64 (d); 7.43 (d); 6.80 (d); 6.75 (d); 6.63 (m); 6.46 (dd); 6.42(sa); 4.40(m); 4.13 (m); 3.92 (m); 3.78(m); 2.31 (m); 1.94 (m); 1.45 (s); 1.18(t).

EXAMPLE 7

(+/-)-Ethyl 7-chloro-4-(1-(4-amino)-phenyl-Δ³-pyrrolin-2-one-3yl)-1,2,3,4-tetrahydroquinoline-2-carboxylate To a solution of example 6 (0.070 g) in ethyl acetate (35 ml) HCl conc.(2.0 ml) was added. The mixture was stirred a rt. under nitrogen atmosphere for 1 h. The mixture was poured into a saturated aqueous solution of NaHCO$_3$ (100 ml) and extracted with EA (200 ml); the organic layer was dried and concentrated in vacuum. The crude mixture was purified by flash chromatography (eluting with CH/EA 1:1) to give the title compound as a yellow solid (0.043 g).

T.l.c. EA R$_f$=0.289. IR:3388 (NH),3161(NH$_2$), 1718 and 1670 (C=O) cm$^{-1}$.

¹H-NMR: 7.36 (d); 6.80 (d); 6.75 (d); 6.56 (m); 6.47 (dd); 6.41(sa); 4.97(m); 4.32 (m); 4.14 (m); 3.91 (m); 3.77(m); 2.31 (m); 1.94 (m); 1.19(t).

EXAMPLE 8

(+/-)-Ethyl 7-chloro-4-(1-(4-acetylamino)-phenyl-Δ³-pyrrolin-2-one-3yl)-1,2,3,4tetrahydroquinoline-2-carboxylate To a solution of example 7 (0.030 g) in pyridine dry (1 ml) Ac$_2$O (0.012 ml) was added. The mixture was stirred at r.t. under nitrogen atmosphere for 30 minutes. The mixture was poured into a saturated aqueous solution of NH$_4$Cl (50 ml) and extracted with EA (50 ml), the organic layer was dried and concentrated in vacuum. The crude mixture was triturated with EA to give the title compound as a white solid (0.025 g)

T.l.c.CH/EA (1:1) R$_f$=0.33. IR:3401(NH), 1730, 1675, 1651 (C=O) cm$^{-1}$. d

¹H-NMR:9.9 (s); 7.69 (d); 7.56 (d); 6.80 (d); 6.75 (d); 665 (m); 6.47 (dd); 6.43 (sa); 4.5–4.37 (m); 4.13 (m); 3.93 (m); 3.79 (m); 2.3–1.94 (m); 2.03 (s); 1.19 (t).

EXAMPLE 9

(+/-)-Ethyl 7-chloro-4-(1-(4-methanesulfonylamino)-phenyl-Δ³-pyrrolin-2-one-3yl)-1,2,3,4-tetrahydroquinoline-2-carboxylate To a solution of example 7 (0.040 g) in CH$_2$Cl$_2$ dry (10 ml) DIPEA (0.021 ml) and CH$_3$SO$_2$Cl (0.008 ml) were added. The mixture was stirred at r.t. under nitrogen atmosphere for 1 h. The mixture was poured onto a saturated aqueous solution of NH$_4$Cl (50 ml) and extracted with EA (50 ml), the organic layer was dried and concentrated in vacuum. The crude mixture was purified by flash chromatography (eluting with CH/EA (1:1) to give the title compound as a yellow solid (0.027 g) .

T.l.c.CH/EA (1:1) R$_f$=0.63. IR:3394(NH, 1726, 1680, 1635 (C=O), (C=C) cm$^{-1}$.

¹H-NMR:7.89 (d); 7.52 (d); 6.81 (d); 6.76 (d); 6.76 (s); 6.47 (dd); 6.45 (sa); 4.52 (m); 4.13 (m); 3.94 (m); 3.81(m); 3.51 (s); 2.3–1.97 (m); 1.19 (t)

EXAMPLE 10

(+)-Ethyl 7-chloro-4-(2-oxo-1-((4tert-butoxycarbonylamino)phenyl-pyrrolidin-3-ylidene)-1,2,3,4-tetrahydro-2-quinolinecarboxylate A solution of intermediate 16 (1.02 g) in dry DMF (100 ml) was stirred in the presence of TEA (0.018 ml) and Pd(PPh$_3$)$_4$ (0.184 g) under a nitrogen atmosphere at 110° C. for 2 h until reaction completion (TLC). The mixture was diluted with a saturated aqueous ammonium chloride solution (100 ml) and EA (200 ml); the organic layer was washed with brine (200 ml), dried and concentrated in vacuum. The crude mixture was purified by flash chromatography (eluting with CH/DCM/EA 5:4:1) to give the title compound (280 mg).

IR:3350 (NH),1718 and 1670 (C=O) cm$^{-1}$. $^1$H-NMR: 9.32 (sa); 759 (d); 7.43 (d); 7.17 (d); 6.94 (d); 6.72 (m); 6.55 (dd); 4.26(dd); 4.19(m); 4.04–3.88 (m); 3.8–3.6 (m); 3.18 (m); 2.942.86 (m); 1.46 (s); 0.92 (t).

EXAMPLE 11

(+)-Ethyl 7-chloro-4-(2oxo-1-(4-amino)phenyl-pyrrolidin-3-ylidene)-1,2,3,4-tetrahydro-2-quinolinecarboxalate To a solution of example 10 (0.280 g) in ethyl acetate (100 ml) HCl conc.(9.5 ml) was added.The mixture was stirred a r.t. under nitrogen atmosphere for 1 h until reaction completion(TIc). The mixture was poured onto a saturated aqueous solution of NaHCO$_3$ (100 ml) and extracted with EA (200 ml); the organic layer was dried and concentrated in vacuum. The crude mixture was triturated with CH/EA 1:1 to give the title compound as a yellow solid (0.191 g).

T.I.c. EA R$_f$=0.33. IR:3464–3406(NH), 3364(NH$_2$), 1730, 1658 and 1633 (C=O) cm$^{-1}$.

$^1$H-NMR: 7.31 (d);7.16 (d); 6.91 (da); 6.71 (d); 655 (d); 6.54 (dd); 5.01(s); 4.26 (dd); 4.17 (m);4.04–3.9 (m); 3.74–3.54(m); 3.14 (m); 2.87 (m);0.96(t).

EXAMPLE 12

(+)-Ethyl 7-chloro-4-(2-oxo-1-(4-acetylamino)phenyl-pyrrolidin-3-ylidene)-1,2,3,4-tetrahydro-2quinolinecarboxylate To a solution of intermediate 19 dry pyridine (1 ml) AC$_2$O (0.010 ml) was added. The mixture was stirred a r.t. under nitrogen atmosphere for 30 minutes. The mixture was poured onto a saturated aqueous solution of NH$_4$Cl (50 ml) and extracted with EA (50 ml), the organic layer was dried and concentrated in vacuum. The crude mixture was triturated with EA to give the title compound as a yellow solid (0.027 g).

T.I.c.CH/EA (1:1) R$_f$=0.63 IR:3396–3325(NH), 1724–1685 (C=O) cm$^{-1}$.

$^1$H-NMR:9.92 (s); 7.62 (d); 7.55 (d);7.16 (d); 6.95 (da); 6.71 (d); 655 (dd); 5.01(s); 4.25 (dd); 4.18 (m);4.1–3.85 (m); 3.77(m); 3.64 (m); 3.18 (m); 2.88 (m); 2.01 (s); 0.91 (t).

EXAMPLE 13

(+)-Ethyl 7chloro-4-(2-oxo-1-((4-methanesulfonyl-amino)phenyl-pyrrolidin-3-ylidene)-1,2,3,4-tetrahydro-2quinolinecarboxylate To a solution of example 12 (0.040 g) in dry CH$_2$Cl$_2$ (10 ml) DIPEA (0.021 ml) and CH$_3$SO$_2$Cl (0.008 ml) were added. The mixture was stirred a r.t. under nitrogen atmosphere for 1 h (TIc). The mixture was poured onto a-saturated aqueous solution of NH$_4$Cl (50 ml) and extracted with EA (50 ml), the organic layer was dried and concentrated in vacuum. The crude mixture was crystallised with CH/EA (1:1) to give the title compound as a yellow solid (0.0239). T.I.c.CH/EA (1:1) R$_f$=0.63.

IR:3384(NH), 1734, 1683 (C=O), 1600 (C=C) cm$^{-1}$.

$^1$H-NMR:7.83 (d); 7.53 (d); 7.21 (d);7.00 (d); 6.75 (d); 6.57 (dd); 4.2–4.3 (m); 4.01 (m); 3.93 (m); 3.87(m); 3.73 (m);3.52(s); 3.22 (m); 3.0–2.9 (m); 0.95 (t).

EXAMPLE 14

(±)-Sodium 7-chloro-4-(1-(3-pyridin)-Δ$^3$-pyrrolin-2-one-3yl)-1,2,3,4-tetrahydroquinoline-2-carboxylate To a solution of example 4a (70 mg) in IMS (5% of methanol in ethanol) (10 ml) a 1N solution of NaOH (0.18 ml) was added and reaction mixture was stirred for 1½ hr. The solvent was evaporated and the crude product was first triturated in methanol/ethyl acetate 05 ml/2 ml then in isopropyl alcohol (3 ml) to yield the title compound (40 mg) as a pale yellow solid.

m.p.>220° C.

NMR (DMSO) δ(ppm) 8.98 (d, 1H), 8.31 (dd, 1H), 8.21 (m, 1H), 7.41 (m, 1H), 6.79 (d, 1H, 6.72 (d, 1H, 6.42 (d, 1H, 6.33 (dd, 1H), 5.71 (s, 1H), 4.50 (m, 1H), 4.44 (m, 1H), 3.76 (m, 1H), 3.11 (m, 1H), 2.27 (m, 1H), 1.43 (m, 1H).

IR (Nujol) (cm$^{-1}$) 3300, 1684.

EXAMPLE 15

(±)-Sodium 7-chloro-4-(1-phenyl-Δ$^3$-5,6-dihydro-pyridin-2one-3yl)-1,2,3,4-tetrahydroquinoline-2-carboxylate To a solution of example 3a (80 mg) in IMS (5% of methanol in ethanol) (6 ml) a 0.1N solution of NaOH (2.9 ml) was added and reaction mixture was stirred for 1 hr. The solution was poured into ethyl acetate and washed with a 1N solution of HCl and brine. The organic phase was dried with Na$_2$SO$_4$ and concentrated to give the crude acid compound. The latter was suspended in ethyl acetate (2 ml) and sodium 2-ethylhexanoate (35 mg) was added obtaining a solution. Diethyl ether (4 ml) and petroleum (3 ml) was added to precipitate the title compound (42 mg) as a white solid.

m.p.>163–166° C.

NMR (DMSO) δ(ppm) 7.4–7.34 (m, 4H), 7.19 (m, 1H), 6.72 (d, 1H), 6.67 (d, 1H), 6.32 (d, 1H), 6.32 (dd, 1H), 5.71 (t, 1H), 5.64 (s, 1H), 3.96 (m, 1H), 3.8–3.65 (m, 2H), 3.17 (dd, 1H), 2.4 (m, 2H), 2.08 (1H, 1.3 (m, 1H)

IR (Nujol) (cm$^{-1}$) 3373, 1658, 1653

EXAMPLE 16

(±)-Sodium 5,7-dichloro-4-(1-phenyl-Δ$^3$-pyrrolin-2-one-3yl)-1,2,3,4-tetrahydroquinoline-2-carboxylate To a solution of example 5 (87 mg) in IMS (5% methanol in absolute ethanol, 5 ml) NaOH (1N, 0.22 ml) was added and stirring continued for 3 hrs. The resulting solution was dried on the rotary evaporator and the resulting solid was triturated with diethyl ether. After filtration and drying the title compound (78 mg) was obtained as an off-white solid.

NMR (DMSO) δ(ppm) 7.80 (m, 2H), 7.38 (t, 2H), 7.10 (t, 1H), 6.82 (d, 1H), 6.46 (d, 1H), 6.37 (s, 1H), 6.11 (s, 1H), 4.42 (s, 2H), 3.98 (d, 1H), 3.05 (dd, 1H, 2.24 (dd, 1H), 1.34 (m, 1H).

IR (Nujol) (cm$^{-1}$) 3385, 1663, 1591, 1555

EXAMPLE 17

(+)Sodium7-chloro-4-(1-phenyl-$\Delta^3$-pyrrolin-2-one-3yl)-1,2,3,4-tetrahydroquinoline-2-carboxylate Method A To a solution of intermediate 13 (110 mg) in THF/H$_2$O (1/1) (3 ml) LiOH (11 mg) was added and stirring continued for 1 h. The resulting solution was concentrated to dryness, taken up with ethyl acetate and 1N HCl was added. After vigorous stirring, the organic phase was separated, washed with water and brine and concentrated. The resulting solid was dissolved in THF (15 ml) and treated with sodium ethylhexanoate (39 mg) for 30 min. After drying, the resulting solid was triturated with hot diethyl ether and filtered, to afford the title compound (69 mg) as a white solid.

e.r.=98%
[α]$_D$=92.5° (c=0.420% w/v in DMSO)
m.p.>200° C.
NMR (DMSO) δ(ppm) 7.80 (m, 2H), 7.39 (m, 2H), 7.11 (m, 1H), 6.80 (d, 1H), 6.72 (d, 1H), 6.36 (d, 1H), 6.34 (dd, 1H), 5.71 (s, 1H), 4.42 (m, 2H), 3.77 (m, 1H), 3.13 (m, 1H), 2.29 (m, 1H), 1.44 (m, 1H).
IR (Nujol) (cm$^{-1}$) 1672, 1600.

Method B

Starting from Example 28 using the procedure as described for Example 21 (Method B).

EXAMPLE 18

(+/−)-7-chloro-4-(1-(4-acetylamino)-phenyl-$\Delta^3$-pyrrolin-2-one-3yl)-1,2,3,4-tetrahydroquinoline-2-carboxylic acid To a solution of example 8 (0.023 g) in IMS (5 ml) NaOH (0.150 ml) was added and the mixture was stirred at rt. for 1 h. The mixture was poured onto a solution of HCl 6N (50 ml) and extracted with EA (50 ml), the organic layer was washed with brine (30 ml), dried and concentrated in vacuum. The crude mixture was triturated with Et$_2$O to give the title compound as a yellow solid (0.019 g). T.I.c. EA R$_f$=0.2.

IR:3401(NH, OH), 1734,1651 (C=O) cm$^{-1}$.
$^1$H-NMR:12.84 (bs); 9.9 (s); 7.69(d); 7.56 (d); 6.80 (d); 6.76 (d);6.6 (d); 6.45 (dd);6.33 (sa); 4.42(m); 3.84–3.78(m); 3.70 (m); 2.3 (m); 2.017 (s); 1.9 (m).

EXAMPLE 19

(+/−)7-chloro-4-(1-(4-methanesulfonylamino)-phenyl-$\Delta^3$-pyrrolin-2-one-3yl)-1,2,3,4-tetrahydroquinoline-2-carboxylic acid To a solution of example 9 (0.027 g) in IMS (5 ml) was added NaOH (0.142 ml). The mixture was stirred a rt. for 2 h. The mixture was poured onto a solution of HCl 6N (50 ml) and extracted with EA (50 ml), the organic layer was washed with brine (30 ml), dried and concentrated in vacuum. The crude mixture was crystallized with CH/EA (1:1) to give the title compound as a yellow solid (0.015 g). T.I.c.

EA R$_f$=0.2. IR:3446(NH,), 1732-(C=O), 1337–1154 (SO$_2$) cm$^{-1}$.
$^1$H-NMR:13–12 (broad); 9.61 (s); 7.75 (d); 7.21 (d); 6.80 (d); 6.76 (d); 6.63 (dd); 6.46 (dd); 6.34 (dd); 4.43(m); 3.85–3.78 (m);2.93 (s); 2.3 (m); 1.92 (m).

EXAMPLE 20

(±)-Sodium 7-chloro-4-(2-oxo-1-phenyl-3-pyrrolidinylidene)-1,2,3,4-tetrahydro-2-quinolinecarboxylate To a solution of example 31b (540 mg) in IMS (5% methanol in absolute ethanol, 7 ml) NaOH (1 N,1.4 ml) was added and stirring continued for 2 hrs. The resulting suspension was filtered and the solid was washed with small portions of diethyl ether. After drying, the title compound (450 mg) was obtained as a yellow solid.

m.p.>200° C..
NMR (DMSO) δ(ppm) 7.74 (d, 2H), 7.37 (t, 2H), 7.11 (t, 1H), 7.12 (d, 1H), 6.77 (d, 1H), 6.38 (dd, 1H), 6.13 (bs, 1H), 4.48 (dd, 1H), 3.78 (m, 2H), 3.2–3.4 (m, 2H), 2.90 (m, 1H), 1.98 (m, 1H)

EXAMPLE 21

(−)odium 7-chloro-4-(2-oxo-1-phenyl-3-pyrrolidinylidene)-1,2,3,4-tetrahydro-2-quinolinecarboxylate Method A To a solution of intermediate 8b (790 mg) in THF/H$_2$O (1/1) (16 ml) LiOH (73 mg) was added and stirring continued for 1 hr. The resulting solution was concentrated to dryness, taken up with ethyl acetate and 1N HCl was added. After vigorous stirring, the organic phase was separated, washed with water and brine and concentrated. The resulting solid was dissolved in THF (15 ml) and treated with sodium ethylhexanoate (265 mg) for 30 mins. After drying, the resulting solid was triturated with hot ethyl acetate and filtered to afford the title compound (400 mg) as a yellow solid.

ee=88.8%
[α]$_D$–603.70 (c=0.316% w/v in DMSO)
m.p.>200° C.
NMR (DMSO) δ(ppm) 7.74 (d, 2H), 7.37 (t, 2H), 7.11 (t, 1H), 7.12 (d, 1H), 6.77 (d, 1H, 6.38 (dd, 1H), 6.13 (bs, 1H), 4.48 (dd, 1H), 3.78 (m, 2H), 3.2–3.4 (m, 2H), 2.90 (m, 1H), 1.98 (m, 1H)
IR (Nujol) (cm$^{-1}$) 3425, 1666,1592

Method B

To a solution of example 27 (3.18 g) in IMS (5% of methanol in ethanol) (100 ml) a 1N solution of NaOH (8.64 ml) was added: the sodium salt precipitates after 5 min. To the resulting suspension diethyl ether was added (50 ml) and the solid was filtered. The solution was evaporated and the solid obtained was mixed to the previous one and triturated with diethylether to afford the title sodium salt (3.2 g) as yellow solid.

m.p.>220° C.
NMR (DMSO) δ(ppm) 7.74 (d, 2H), 7.37 (t, 2H), 7.11 (t, 1H); 7.11 (d, 1H); 6.76 (d, 1H); 6.38 (dd, 1H); 6.11 (s, 1H); 4.48 (dd, 1H); 3.78 (m, 2H); 3.4–3.2 (m, 2H); 2.9 (m, I H); 1.95 (m, 1H).
IR (Nujol) (cm$^{-1}$) 3392, 1669.
[α]–603.7°(c=0.316%w/v in DMSO)
e.e.: 96%

Method C 125 g of *Aspergillus niger* lipase (Amano AP12) were suspended in 650 ml of 100 mM calcium chloride solution in a stirred reactor. The suspension was cooled to 15° C. 50 g of example 31b were then dissolved in dimethyl sulphoxide (350 ml) and this solution added to the reactor. The reactor was then heated to 37° C. and the mixture stirred for 24 hours. The reactor temperature was then lowered to 20° C. and 1 liter of 0.2M hydrochloric acid was slowly added to the reactor. The reactor was then emptied and 50 g of filter aid (Dicalite) were added to the reaction mixture. The mixture was then filtered and the filter cake washed with water, before being dried. A 20 g sample of dried filter cake was dispersed in 390 ml of methyl t-butyl ether and 10 ml of 2M hydrochloric acid were added. This was stirred for 3 hours and filtered, the filter cake was washed with 100 ml of methyl t-butyl ether. The product was back extracted from the methyl t-butyl ether 500 into ml of 0.05M sodium hydroxide solution. The aqueous layer was then separated, acidified with 6 ml of 5M hydrochloric acid and the product extracted into 500 ml ethyl acetate. The ethyl acetate was removed by evaporation and the residue dissolved in IMS (80 ml). The title compound was identified in this solution by HPLC assay as follows:

0.5 ml reaction mixture diluted into 2 mls DMSO and mixed to dissolve. 5 ul of this further diluted ino 1 ml of mobile phase (70% acetonitrile in 20 mM Amnmonium acetate pH 3.0),Column: Sphersorb C6 50×4.6 mm, Flow rate: 1 ml/min, Detection: uv adsorbance at 254 nm, Injection vol: 10 ul, Retention time: 0.8 min. The solution was diluted to 96 ml with IMS and stirred while 10 ml of 1 M sodium hydroxide were added drop-wise over 15 minutes. 40 ml of diethyl ether were added over 10 minutes and stirring continued for 1 hour. The mixture was then placed in the fridge for 1 hour and the product filtered, washed with 50 ml of cold diethyl ether before being dried overnight under vacuum to obtain the title compound (3.3 g). HPLC analyses: the title compound was dissolved in DMSO at 1 mg/ml. 10 ul of this diluted into 990 ul of mobile phase.

Colomn: Phenomenex Luna Phenyl hexyl 150×4.6 mm, Injection vol: 50 ul, Retention time: 3.4 min.

EXAMPLE 22

(±)-Sodium 7-chloro-4-(2-oxo-1-(pyridn-3yl)-pyrrolidin-3-ylidene)-1,2,3,4-tetrahydro-2-quinolinecarboxylate To a solution of example 4b (55 mg) in IMS (5% of methanol in ethanol) (10 ml) a 1N solution of NaOH (0.145 ml) was added and reaction mixture was stirred for 1½ hr. The solvent was evaporated and the crude product was triturated in ethyl acetate 2 ml to yield the title compound (38 mg) as a yellow solid.

m.p.>220° C.

NMR (DMSO) δ(ppm) 8.96 (d, 1H, 8.32 (dd, 1H, 8.18 (m, 1H), 7.40 (m, 1H), 7.12 (d, 1H), 6.78 (d, 1H), 6.38 (dd, 1H), 6.15 (s, 1H), 4.46 (m, 1H), 3.83 (m, 2H), 3.3–3.2 (m, 2H), 2.92 (m, 1H), 1.97 (m, 1H).

IR (Nujol) (cm$^{-1}$) 3361, 1669.

EXAMPLE 23

(±)-7-chloro-4-(2-oxo-1-phenyl-3-piperidinylidene)-1,2,3,4-tetrahydro-2quinolinecarboxylic acid To a solution of example 3b (48 mg) in IMS (5% of methanol in ethanol) (2 ml) a 0.1N solution of NaOH (1.2 ml) was added and reaction mixture was stirred for 2½ hr. The solution was poured into ethyl acetate and washed with a 1N solution of HCl and brine. The organic phase was dried and concentrated to give the crude product which was triturated in ethyl acetate/petroleum 2 ml/5 ml, to yield the title compound (14 mg) as a yellow solid.

m.p.>130–133° C.

NMR (DMSO) δ(ppm) 12.64 (s, 1H), 7.38 (t, 2H), 7.30 (d, 2H), 7.22 (t, 1H), 6.99 (d, 1H), 6.87 (bd, 1H), 6.67 (d, 1H), 6.50 (dd, 1H), 4.08 (m, 1H), 3.54 (m, 2H), 3.43 (m, 1H), 2.83 (m, 1H), 2.72 (m, 1H), 2.58 (1H), 1.93–1.8 (m, 2H)

IR (Nujol) (cm$^{-1}$) 3348, 1732, 1717
MS (m/z) 383

EXAMPLE 24

(±)-7-chloro-4-(2,5-dioxo-1-phenyl-imidazolidin-4-ylidene)-1,2,3,4-tetrahydro-2-quinolinecarboxylic acid To a solution of intermediate 18 (10 mg) in $CH_2Cl_2$ (5 ml) a 1M solution of $BCl_3$ in hexane (0.1 ml) was added at −78° C. and reaction mixture was stirred for 1½ hr maintaining the temperature between −20 and −10° C. The solution was poured into ethyl acetate and washed with a 3N solution of HCl and brine. The organic phase was dried with $Na_2SO_4$ and concentrated to give the crude product which was triturated in diethyl ether/petroleum (1 ml/3 ml), to yield the title compound (6 mg) as a yellow solid.

m.p.>190° C. deg.

NMR (DMSO) δ(ppm) 12.75 (bs, 1H), 10.50 (bs, 1H), 7.50–7.39 (m, 6H), 6.99 (bs, 1H), 6.76 (d, 1H), 6.57 (dd, 1H), 4.15 (m, 1H), 3.77.(m, 1H), 3.17 (dd, $_1$H,.

IR (Nujol) (cm$^{-1}$) 3400, 2800, 1746, 1701

EXAMPLE 25

(+/−)-7-chloro-4-(2-oxo-1-(4-acetylamino)phenyl-pyrrolidin-3-ylidene)-1,2,3,4-tetrahydro-2-quinolinecarboxylic acid To a solution of example 12 (0.027 g) in THF $H_2O$ (3:1) (10 ml) was added LiOH (0.010 g). The mixture was stirred a rt. for 1 h. The mixture was poured onto a saturated aqueous solution of $NH_4Cl$ (50 ml) and extracted with EA (50 ml), the organic layer was washed with brine (30 ml), dried and concentrated in vacuum. The crude mixture was triturated with EA to give the title compound as a yellow solid (0.020 g). T.I.c.CH/EA (1:1) R$_f$=0.2. IR:3400–2700 (NH, OH), 1660 (C=O) cm$^{-1}$.

$^1$H-NMR:12.63 (sa); 9.94 (sa); 7.65(d); 7.58 (d); 7.20 (d); 6.83 (sa); 6.74 (d); 654 (dd); 4.03(m); 3.78(m); 3.70 (m); 3.2–2.6 (m); 2.03 (s).

EXAMPLE 26

(+/−)7-chloro-4-(2-oxo-1-((4methanesulfonyl amino)phenyl-pyrrolidin-3-ylidene)-1,2,3,4-tetrahydro-2-quinolinecarboxylic acid To a solution of example 13 (0.023 g) in IMS (5 ml) NaOH (0.120 ml) was added. The mixture was stirred a r.t. for 2 h. The mixture was poured onto a solution of HCl 6N (50 ml) and extracted with EA (50 ml), the organic layer was washed with brine (30 ml), dried and concentrated in vacuum. The crude mixture was chromatographed with $Et_2O$ to give the title compound as a yellow solid (0.007 g). T.I.c.CH/EA (1:1) R$_f$=0.2.

IR:3411 (NH,), 1692,1651–1583 (C=O), (C=C), 1306–1154 ($SO_2$) cm$^{-1}$.

$^1$H-NMR: 9.65 (s); 7.69(d); 7.22 (d); 7.20 (d); 6.73 (d); 655 (dd); 4.03(m); 3.8–3.5 (m); 3.3–2.9 (m); 2.9 (s).

EXAMPLE 27

7-chloro-4-(2-oxo-1-phenyl-3-pyrrolidinylidene)-1,2,3,4-tetrahydro-2-quinolinecarboxylic acid (enantiomer A)

To a solution of intermediate 22 (6.2 g) in THF1H$_2$O (100 ml, 3/1) at room temperature LiOH (1 g) was added and stirring continued for 1 hr. The THF was evaporated and $H_2O$ (100 ml) was added. The resulting solution was washed with diethylether (2×50 ml). The aqueous phase was acidified until pH=4 with HCl 10% and the product extracted with ethyl acetate (2×100 ml) The organic phase was washed with water and brine, dried and evaporated to afford the title compound (4.2 g) as a yellow solid. m.p.>200° C.

NMR (DMSO) δ(ppm) 12.62 (bs, 1H; 7.72 (d, 2H), 7.38 (t, 2H), 7.20 (d, 1H), 7.13 (t. 1H), 6.86 (d, 1H), 6.74 (d, 1H), 6.54 (dd, 1H), 4.06 (m, 1H), 3.86–3.68 (m, 3H), 3.3 (m, 1H), 3.18–2.88 (m, 2H).

IR (nujol): 3356, 1724

EXAMPLE 28

7Chloro4-(2-oxo-1-phenyl-Δ3-pyrrolin-2-one-3-yl)-1,2,3,4-tetrahydroquinoline-2-carboxylic acid; (enantiomer A)

To a solution of intermediate 10 (1.289 g) in THF/$H_2O$ (30 ml, 311) at room temperature LiOH (0.24 g) was added and stirring continued for 1 hr. The THF was evaporated and $H_2O$ (80 ml) was added. The resulting solution was washed with diethylether (2×50 ml). The aqueous phase was acidified until pH=4 with HCl 10% and the product was filtered and washed with water (10 ml). The product was dried under vacuum at 60 C. for 12 hrs to obtain 0.734 g as white solid.

m.p.: 190° C.

e.e.: 100%

NMR (DMSO) δ(ppm) 12.86 (bs, 1H); 7.79 (d, 2H), 7.38 (t, 2H), 7.11 (d, 1H), 6.81 (d, 1H), 6.77 (d, 1H), 6.64 (s, 1H), 6.46 (dd, 1H); 6.34 (s, 1H); 4.46 (m, 1H), 3.82–3.79 (m, 2H), 2.34 (m, 1H); 1.92 (m, 1H).

IR (nujol): 3356, 1724

EXAMPLE 29

Sodium, 5,7-Dichloro-4-(2-oxo-1-phenyl-Δ3-pyrrolin-2-one-3-yl)-1,2,3,4-tetrahydroquinoline-2-carboxylic acid; (enatiomer A)

To a solution of intermediate 26a (0.35 g) in THF/$H_2O$ (10 ml, 3/1) at room temperature LiOH (0.069) was added and stirring continued for 30 min. The THF was evaporated and $H_2O$ (5 ml) was added. The resulting solution was washed with diethylether (2×50 ml). The aqueous phase was acidified until pH=4 with HCl 10% and the product filtered and dried under vacuum at 60 C. for 12 hrs to afford the title compound (0.134 g) as white solid. The solid was dissolved in IMS (5% of methanol in ethanol) (10 ml) and a 1N solution of NaOH (0.33 ml) was added. To the resulting suspension diethyl ether was added (10 ml) and the solid was filtered, washed with diethyl ether (10 ml) and dried under vacuum for 12 hrs to give the title compound (0.082 g) as a white solid.

m.p.>220° C.

NMR ($D_2O$) δ(ppm) 7.49 (d, 2H); 7.40(t, 2H); 7.23 (t, 1H); 6.74 (d, 1H); 6.70 (d, 1H); 6.51 (m, 1H); 4.404.35 (m, 2H); 4.11 (m, 1H); 3.53 (dd, 1H); 2.18 (m, 1H); 1.74 (td, 1H)

HPLC Column: Cyclobond I, R,S-Hydroxypropyl ether 25 cm×4.6 mm; Mobile Phase: Methanol=50 20 mM Ammonium Acetate buffer pH 5=50% by volume; Flow rate: 1 ml/min; Retention time: 12 mins.

EXAMPLE 30

Sodium 5,7-dichloro-4-(2-oxo-1-phenyl)-pyrrolidin-3-ylidene)-1,2,3,4-tetrahydro-2-quinoline carboxylate(enatiomer A)

To a solution of intermediate 26b (0.052 g) in THF/$H_2O$ (4 ml, 3/1) at room temperature LiOH (0.001 g) was added and stirring continued for 30 min. The THF was evaporated and $H_2O$ (2 ml) was added. The resulting solution was washed with diethylether (2×50 ml). The aqueous phase was acidified until pH=4 with HCl 10% and the product was filtered and washed with water (10 ml) and was dried under vacuum at 60° C. for 12 hrs to obtain 5,7-dichloro-4-(2-oxo-1-(pyridn-3yl)-pyrrolidin-3-ylidene)-1,2,3,4-tetrahydro-2-quinoline carboxylic acid 0.033 g as a yellow solid. The solid was dissolved in IMS (5% of methanol in ethanol) (5 ml) and a 1N solution of NaOH (0.08 ml) was added. After 5 min, the solvent was evaporated and the solid triturated with diethyl ether (5 ml), filtered, dried under vacuum for 12 hrs to give the title compound (0.01 g) as a yellow solid.

m.p.: >200°

NMR (DMSO) δ(ppm) 7.74 (d, 2H); 7.39 (t, 2H); 7.15 (t, 1H); 6.76 (d, 1H); 6.51 (d, 1H); 6.20 (m, 1H); 4.63 (dd, 1H; 3.78 (m, 2H); 3.41 (dd, 1H); 3.18 (m, 1H); 2.35 (dd, 1H; 1.81 (t, 1H).

IR (nujol): 3363, 1688, 1630, 1586 $cm^{-1}$

EXAMPLE 31

(±)-Ethyl 7-chloro-4-(1-phenyl-Δ$^3$-pyrrolin-2-one-3yl)-1,2,3,4-tetrahydroquinoline-2-carboxylate (31a)

(±)-Ethyl 7-chloro-4-(2-oxo-1-phenyl-3-pyrrolidinylidene)-1,2,3,4-tetrahydro-2-quinolinecarboxylate (31 b)

To a solution of intermediate 4 (2.2 g) in DMF (50 ml) Pd(PPh$_3$)$_4$ (244 mg) and TEA (1.2 ml) were added and the resulting solution was heated to 110° C. for 2 h. The crude solution was poured into 200 ml of ethyl acetate and washed first with a saturated solution of NH$_4$Cl (2×150 ml), then with water and brine. The organic phase was dried and concentrated to give the crude product. Purification by column chromatography (cyclohexane-/dichloromethane/ethyl acetate 50/40/10) Rf=0.41 gave the title compound 31a (540 mg) as an off-white solid.

m.p.=150–153° C.

NMR (DMSO) δ(ppm) 7.80 (m, 2H), 7.39 (m, 2H), 7.12 (m, 1 H), 6.83 (d, 1H), 6.77 (d, 1H), 6.69 (m, 1H), 6.48 (dd, 1H), 6.45 (s, 1H), 4.48 (m, 2H), 4.15 (m, 2H), 3.94 (m, 1H), 3.82 (m, 1H), 2.34 (m, 1H), 1.97 (m, 1H), 1.20 (t, 3H)

IR (Nujol) ($cm^{-1}$) 3385, 1728, 1680 and the title compound 31b (475 mg) R$_f$=0.29 as a yellow solid. p m.p.=152–156° C.

NMR (DMSO) δ(ppm) 7.72 (m, 2H), 7.39 (m, 2H), 7.20 (d, 1H), 7.16 (m, 1H), 6.98 (d, 1H), 6.74 (d, 1H, 6.57 (dd, 1H, 4.29 (dd, 1H), 4.21 (m, 1H), 4.02 (m, 1H), 3.93 (m, 1H), 3.82 (m, 1H), 3.69 (m, 1H), 3.20 (m, 1H, 2.92 (m, 2H), 0.93 (t, 3H)

EXAMPLE 31a (±)-Ethyl 7-chloro-(4-phenyl-Δ$^3$-pyrrolin-2-1,2,3,4-tetrahydroquinoline-2-carboxylate To a solution of intermediate 4a (0.1 g) in dry DMF (5 ml) Pd(OAc)2 (10 mg) and TEA (0.026 ml) were added. The mixture was heated at 110 C. for 2 hrs, then diluted with a saturated solution of NH4Cl and extracted with ethyl acetate (2×10 ml). The solvent was evaporated and the crude purified by flash chromatography (Cyclohexane/EA 8:2) to afford the title compound as a white solid (40 mg).

EXAMPLE 31b (±)-Ethyl 7-chloro-4-(2-oxo-1-phenyl-3-pyrrolidinylidene)-1,2,3,4-tetrahydro-2-quinolinecarboxylate To a solution of intermediate 4b (370 g) in toluene (5.2 lit), Triethylamine (248 ml), Triphenilphosphine (7.4 g) and PdCl$_2$ (2.52 g) were added. The resulting solution was warmed to 100° C. and stirred for 2 h. The suspension was chilled to 20–25° C. and toluene (2.6 ml) was added. The reaction mixture was washed with NH$_4$Cl 8% (3×5.2 lit) and water (5.2 lit). The organic layer was filtered over a celite pad and it was washed with toluene (1 lit); then it was distilled under vacuum (T=50° C.; P=60 mbar) to reach 6.3 lit. After cooling to T=20–25° C., isooctane (5.2 lit) was dropped over 30 min. The precipitate was stirred for 2 h 30 min then it was filtered and washed with a mixture toluene/isooctane 1/1 (1.85 lit). The yellow solid was dried in vacuum at T=40° C. for 18 h to obtain the title compound as a yellow solid 210 g.

m.p. 160–162° C.

NMR (DMSO): 7.72 (m, 2H); 7.39 (m, 2H); 7.20 (d, 2H); 7.15 (m, 2H); 6.96 (dd, 1H); 6.74 (d, 1H); 6.57 (dd, 1H); 4.29 (dd, 1H); 4.21 (m, 1H); 4.02 (m, 1H); 3.93 (m, 1H; 3.82 (m, 1H); 3.69 (m, 1H); 3.20 (m, 1H). 2.92 (m, 2H); 2.92 (m, 2H); 0.93 (t. 3H).

Pharmacy Examples

| A. Capsules/Tablets | |
|---|---|
| Active ingredient | 20.0 mg |
| Starch 1500 | 2.5 mg |
| Microcrystalline Cellulose | 200.0 mg |
| Croscarmellose Sodium | 6.0 mg |
| Magnesium Stearate | 1.5 mg |

The active ingredient is blended with the other excipients. The blend can be used to fill gelatin capsules or compressed to form tablets using appropriate punches. The tablets can be coated using conventional techniques and coatings.

| B. Tablets | |
|---|---|
| Active ingredient | 20.0 mg |
| Lactose | 200.0 mg |
| Microcrystalline Cellulose | 70.0 mg |
| Povidone | 25.0 mg |
| Croscarmellose Sodium | 6.0 mg |
| Magnesium Stearate | 1.5 mg |

The active ingredient is blended with lactose, microcrystalline cellulose and part of the croscarmellose sodium. The blend is granulated with povidone after dispersing in a suitable solvent (i.e. water). The granule, after drying and comminution is blended with the remaining excipients. The blend can be compressed using appropriate punches and the tablets coated using conventional techniques and coatings.

| c) Bolus | |
|---|---|
| Active ingredient | 0.1–32 mg/ml |
| Sodium phosphate | 1.0–50.0 mg/ml |
| water for injection qs to | 1 ml |

The formulation may be packed in glass ampoules or vials and syringes with a rubber stopper and a plastic/metal overseal (vials only).

| D) Infusion | |
|---|---|
| Active ingredient | 0.01–3.2 mg/ml |
| 5% dextrose injection qs to | 100 ml |

The formulation may be packed in glass vials or plastic bag.

The affinity of the compound of the invention for the strychnine insensitive glycine binding site was determined using procedure of Kishimoto H. et al J.

The pki values obtained with representative compounds of the invention are given in the following table:

| Example No | pki |
|---|---|
| 1 | 8.1 |
| 14 | 7.9 |
| 15 | 7.73 |
| 16 | 7.8 |
| 17 | 8.7 |
| 18 | 7.78 |
| 19 | 8.9 |
| 21 | 7.1 |
| 22 | 7.9 |
| 24 | 7.8 |
| 25 | 7.15 |
| 30 | 7.7 |
| 29 | 8.7 |

The ability of compounds of the invention to inhibit pain in mouse has been assessed in the formalin test as described by Dubuisson and Dennis (*Pain*, 1977, 4:161–174). In this test 20 μl of 1% formalin was injected into the plantar surface of the mouse left hind paw. The amount of time, in seconds, the animals spent licking the injected paw for the first 5 minutes (early phase) and then from 20 to 60 minutes (late phase) after formalin was used as measurement of the intensity of pain. The compounds of the invention were administered orally 1 hour before formalin injection.

From these results the dose required to reduce the licking time by 50% expressed as mg/kg is referred to as the ED$_{50s}$ value. Representative results obtained for compounds of the invention when given by oral administration are given in the following table:

| Ex No | ED$_{50}$ (mg/kg po) |
|---|---|
| 21 | 0.14 |
| 17 | 0.3 |
| 2 | 0.03 |

No untoward effects have been observed when compounds of the invention have been administered to mice at pharmacologically active doses.

What is claimed is:

1. (−)7-chloro-4-(2-oxo-1-phenyl-3-pyrrolidinylidene)-1,2,3,4-tetrahydro-2-quinoline carboxylic acid, and physiologically acceptable salts and non-toxic metabolically labile esters thereof.

2. A pharmaceutical composition comprising (−)-7-chloro-4-(2-oxo-1-phenyl-3-pyrrolidinylidene)-1,2,3,4-tetrahydro-2-quinoline carboxylic acid, or a physiologically acceptable salt or non-toxic metabolically labile ester thereof.

3. The pharmaceutical composition according to claim 2, further comprising one or more physiologically acceptable carriers or excipients.

4. A method for the treatment of a mammal for conditions where antagonising the effects of excitatory amino acids on the NMDA receptor complex is of therapeutic benefit, said method comprising administration of an effective amount of (−)7-chloro-4-(2-oxo-1-phenyl-3-pyrrolidinylidene)-1,2,3,4-tetrahydro-2-quinoline carboxylic acid, or a physiologically acceptable salt or non-toxic metabolically labile ester thereof.

5. A method for selectively antagonising the strychnine insensitive glycine binding site associated with the NMDA receptor complex, said method comprising administration of (−)7-chloro-4-(2-oxo-1-phenyl-3-pyrrolidinylidene)-1,2,3,4-tetrahydro-2-quinoline carboxylic acid, or a physiologically acceptable salt or non-toxic metabolically labile ester thereof.

6. A method for the treatment or prophylaxis of neurotoxic damage or neurodegenerative diseases, said method comprising administration of (−)7-chloro-4-(2-oxo-1-phenyl-3-pyrrolidinylidene)-1,2,3,4-tetrahydro-2-quinoline carboxylic acid, or a physiologically acceptable salt or non-toxic metabolically labile ester thereof.

7. A method for the treatment or prophylaxis of migraine in a subject in need thereof, said method comprising administration of (−)-7-chloro-4-(2-oxo-1-phenyl-3-pyrrolidinylidene)-1,2,3,4-tetrahydro-2-quinoline carboxylic acid, or a physiologically acceptable salt or non-toxic metabolically labile ester thereof.

8. A method for the treatment or prophylaxis of withdrawal symptoms from nicotine in a subject in need thereof, said method comprising administration of (−)7-chloro-4-(2-oxo-1-phenyl-3-pyrrolidinylidene)-1,2,3,4-tetrahydro-2-quinoline carboxylic acid, or a physiologically acceptable salt or non-toxic metabolically labile ester thereof.

9. A method for the treatment or prophylaxis of withdrawal symptoms from alcohol in a subject in need thereof, said method comprising administration of (−)7-chloro-4-(2-oxo-1-phenyl-3-pyrrolidinylidene)-1,2,3,4-tetrahydro-2-quinoline carboxylic acid, or a physiologically acceptable salt or non-toxic metabolically labile ester thereof.

10. A method for the treatment or prophylaxis of withdrawal symptoms from alcohol comprising administration of an effective amount of a compound of formula (I):

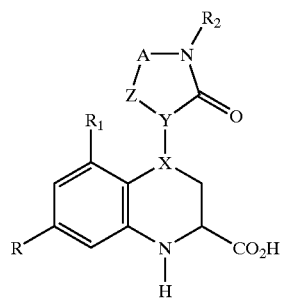

(I)

or a salt or a non-toxic metabolically labile ester thereof, wherein

Y is a carbon atom;

Z is the group CH which is linked to the group Y via a double bond and X is CH, or Z is methylene or $NR_{11}$ and X is a carbon atom linked to the group Y via a double bond;

A is $C_{1-2}$ alkylene chain optionally substituted by one or two groups selected from the group consisting of =O and $C_{1-6}$alkyl optionally substituted by hydroxy, amino, $C_{1-4}$ alkyl amino or $C_{1-4}$dialkyl amino;

R is a halogen atom or $C_{1-4}$alkyl group;

$R_1$ is a hydrogen, a halogen atom or $C_{1-4}$alkyl group;

$R_2$ is selected from the group consisting of phenyl optionally substituted with up to 3 groups selected from the group consisting of halogen, hydrogen, or $(CH_2)_nR_3$ wherein $R_3$ is $COR_4$, $NR_6R_5$, $NHCOR_7$, $NHCONR_9R_8$ or $NHSO_2R_{10}$; a 5 membered heteroaryl group containing 1 to 3 heteroatoms selected from the group consisting of oxygen, sulphur and nitrogen; and a 6 membered heteroaryl group containing 1 to 3 nitrogen atoms $R_4$ is an amino, a hydroxyl or $C_{1-4}$ alkoxy group;

$R_5$ and $R_6$ are each independently hydrogen or $C_{1-4}$alkyl group or $R_5$ and $R_6$ together with the nitrogen atom to which they are attached represent a saturated 5–7 membered heterocyclic group optionally containing an additional heroatom selected from oxygen, sulphur and nitrogen $R_7$ is a hydrogen atom, $C_{1-4}$alkyl, $C_{1-4}$alkoxy, or phenyl;

$R_8$ is hydrogen or $C_{1-4}$alkyl group;

$R_9$ is hydrogen, $C_{1-4}$alkyl optionally substituted by one or more of hydroxy, carboxyl or amino groups, or phenyl;

$R_{11}$ is hydrogen or $C_{1-4}$alkyl group;

$R_{10}$ is hydrogen, $C_{1-4}$alkyl or a nitrogen protecting group; and n is 0, 1 or 2.

* * * * *

UNITED STATES PATENT AND TRADEMARK OFFICE
CERTIFICATE OF CORRECTION

PATENT NO. : 6,413,985 B1
DATED : July 2, 2002
INVENTOR(S) : Di Fabio et al.

It is certified that error appears in the above-identified patent and that said Letters Patent is hereby corrected as shown below:

<u>Title page,</u>
Item [73], Assignee, "SmithKline Beecham Corporation, Philadelphia, PA" should be
-- GlaxoSmithKline SPA, Via Alessandro Fleming, 2,37135 Verona, Italy --

Signed and Sealed this

Twenty-seventh Day of April, 2004

JON W. DUDAS
*Acting Director of the United States Patent and Trademark Office*